United States Patent [19]
Lafontaine et al.

[11] Patent Number: 5,964,782
[45] Date of Patent: Oct. 12, 1999

[54] CLOSURE DEVICE AND METHOD

[75] Inventors: Daniel M. Lafontaine, Plymouth; Kent D. Harrison, Maple Grove, both of Minn.

[73] Assignee: SciMed Life Systems, Inc., Maple Grove, Minn.

[21] Appl. No.: 08/932,990

[22] Filed: Sep. 18, 1997

[51] Int. Cl.[6] .................................................. A61B 17/04
[52] U.S. Cl. .......................... 606/213; 606/139; 606/143; 606/149
[58] Field of Search .................................... 606/149, 139, 606/213, 148, 144

[56] References Cited

U.S. PATENT DOCUMENTS

| | | | |
|---|---|---|---|
| 3,908,662 | 9/1975 | Razgulov et al. | 606/149 |
| 5,234,447 | 8/1993 | Kaster et al. | 606/213 |
| 5,364,408 | 11/1994 | Gordon | 606/144 |
| 5,478,353 | 12/1995 | Yoon | 606/213 |
| 5,776,152 | 7/1998 | Sekons | 606/148 |
| 5,782,861 | 7/1998 | Cragg et al. | 606/216 |
| 5,817,110 | 10/1998 | Kronner | 606/149 |

*Primary Examiner*—Gary Jackson
*Attorney, Agent, or Firm*—Crompton, Seager & Tufte

[57] ABSTRACT

An apparatus is provided for closing a perforation in a wall of a patient's blood vessel or other organs, and a method of introducing the apparatus and causing the closure are described. The apparatus includes an elongated support member having a distal end supporting one or more tissue engaging hooks configured to engage fibrous vessel tissue when moved in a first direction and to disengage the tissue when moved in a second direction, and a proximal end for applying rotational torque to the support member to cause the hooks to engage collagen fibrous tissue in the adventitia of the blood vessel or fibrous tissue in other body organs. The hooks engaging the collagen fiber causes the blood vessel tissue surrounding the perforation to be drawn into close proximity such that the perforation can be closed. The apparatus can be removed by applying reverse rotation of the support member, whereby the hooks are disengaged. The apparatus is deployed in an outer sheath with the hooks encased until a selected engaging location has been achieved. When positioned in the aperture to be closed, the hooks are exposed to allow interaction with the adventitia. Puncture closure can be accomplished by various techniques, including stasis, cauterizing, or by clamping. Various embodiments of the apparatus are described.

55 Claims, 14 Drawing Sheets

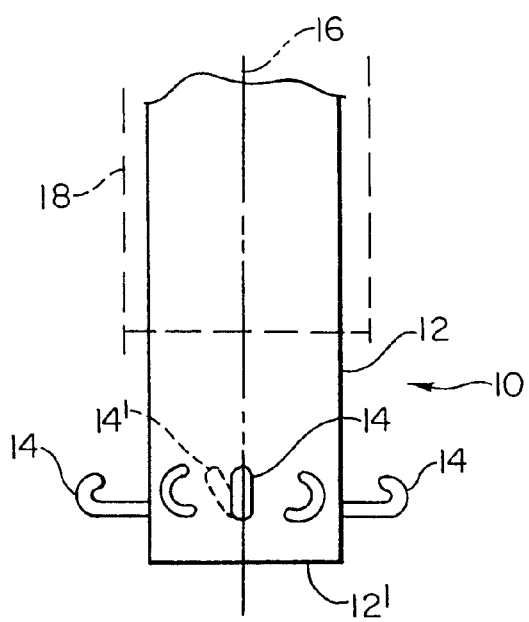
Fig. 1
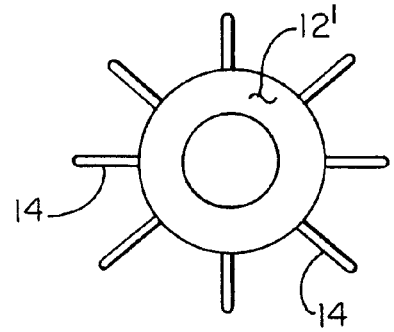
Fig. 2
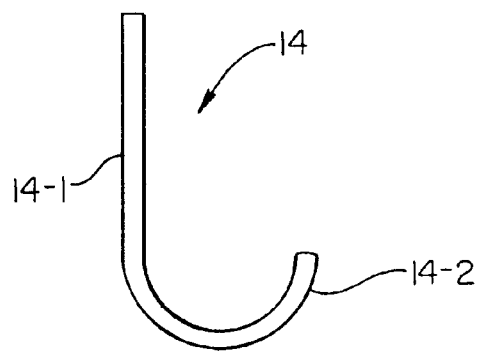
Fig. 3A
Fig. 3B
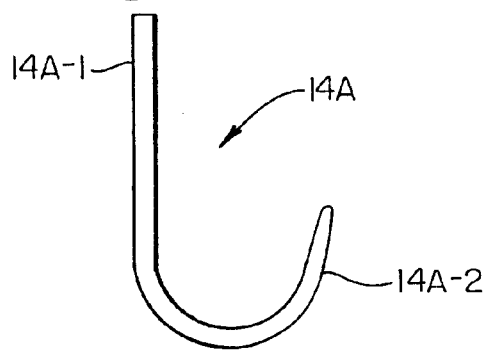
Fig. 4A
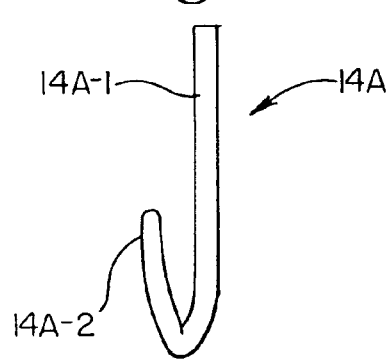
Fig. 4B

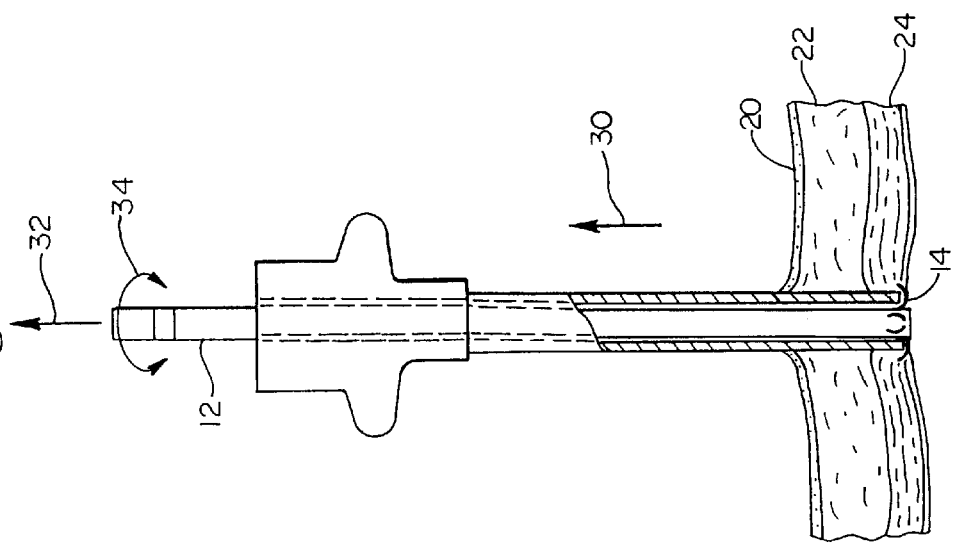
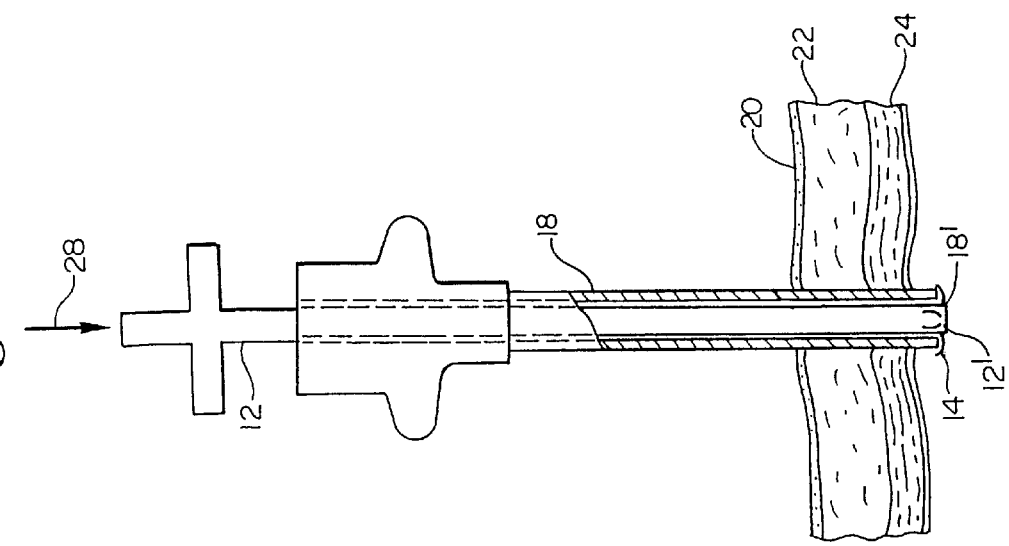
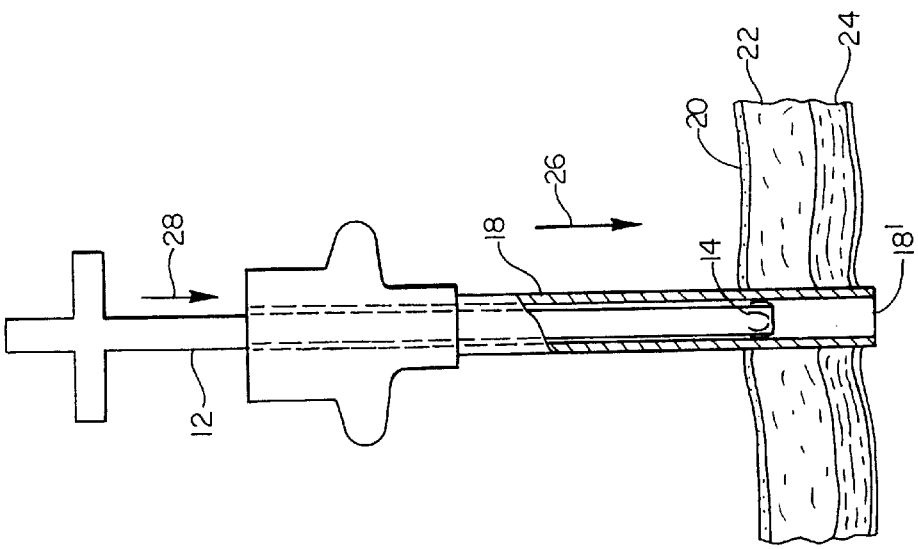

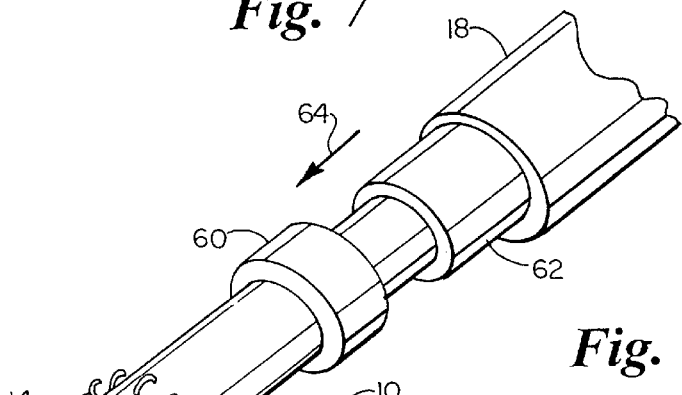
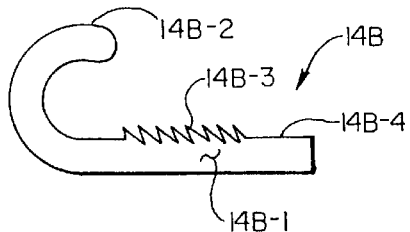
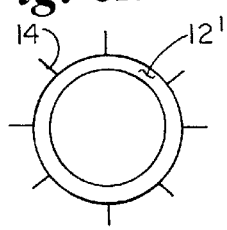
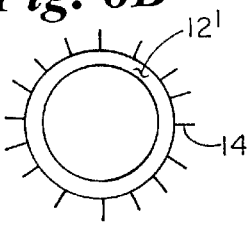
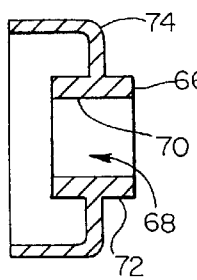
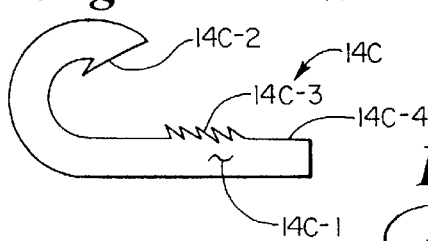
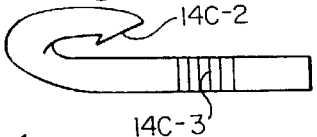
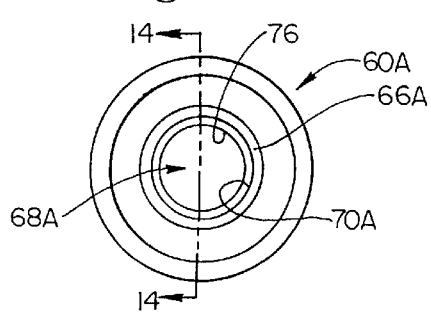
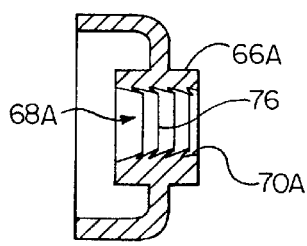

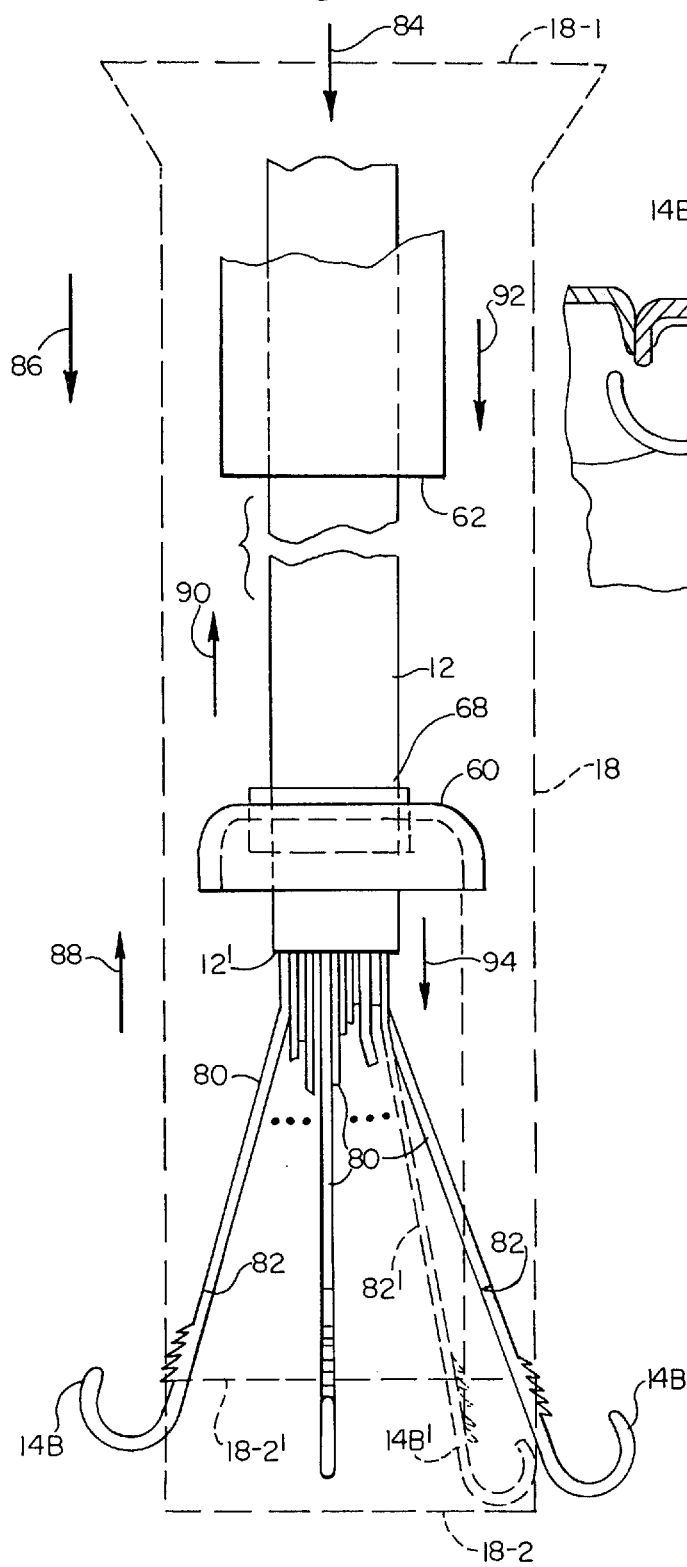
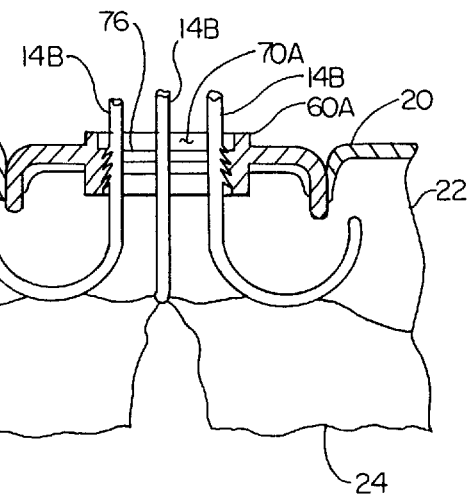
Fig. 15
Fig. 16

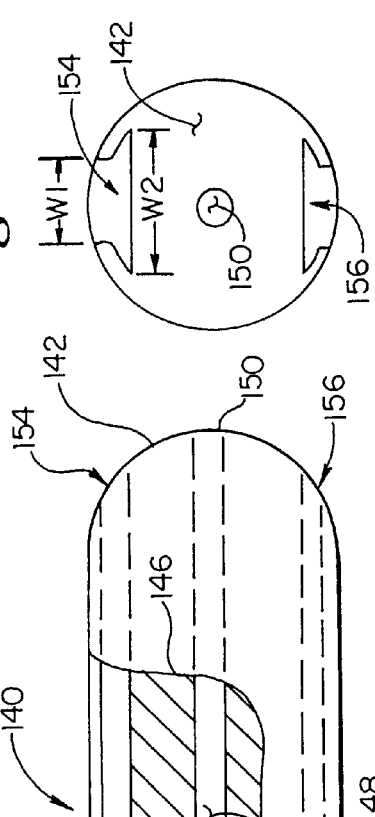
*Fig. 22*
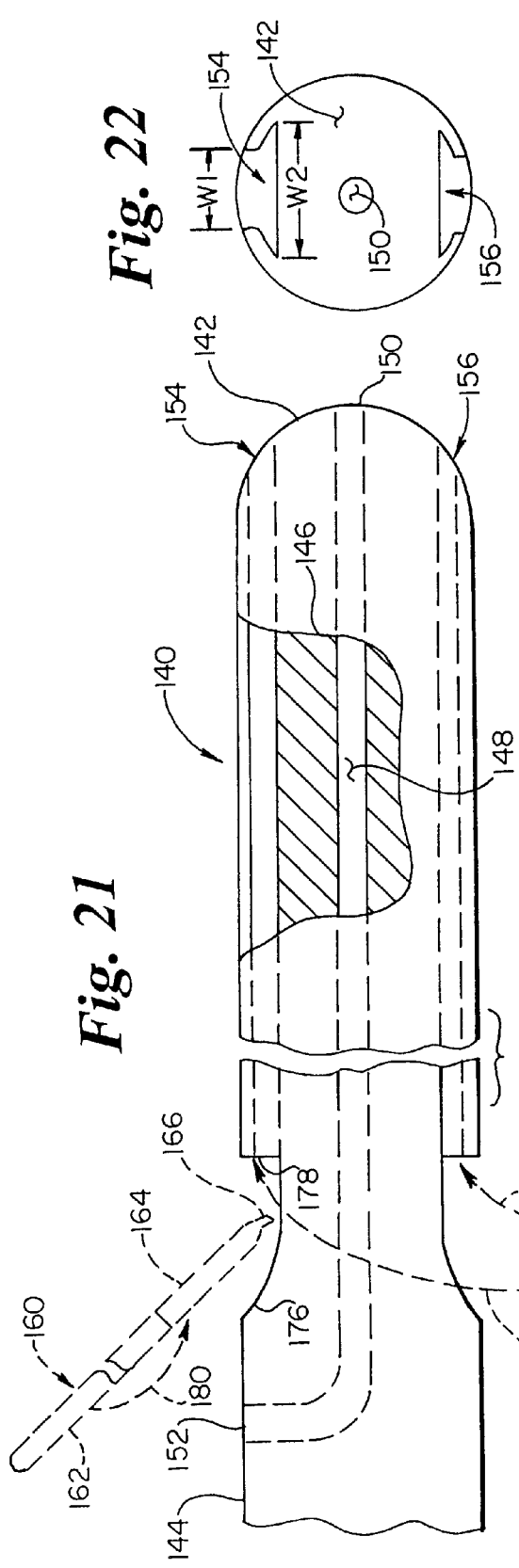
*Fig. 21*
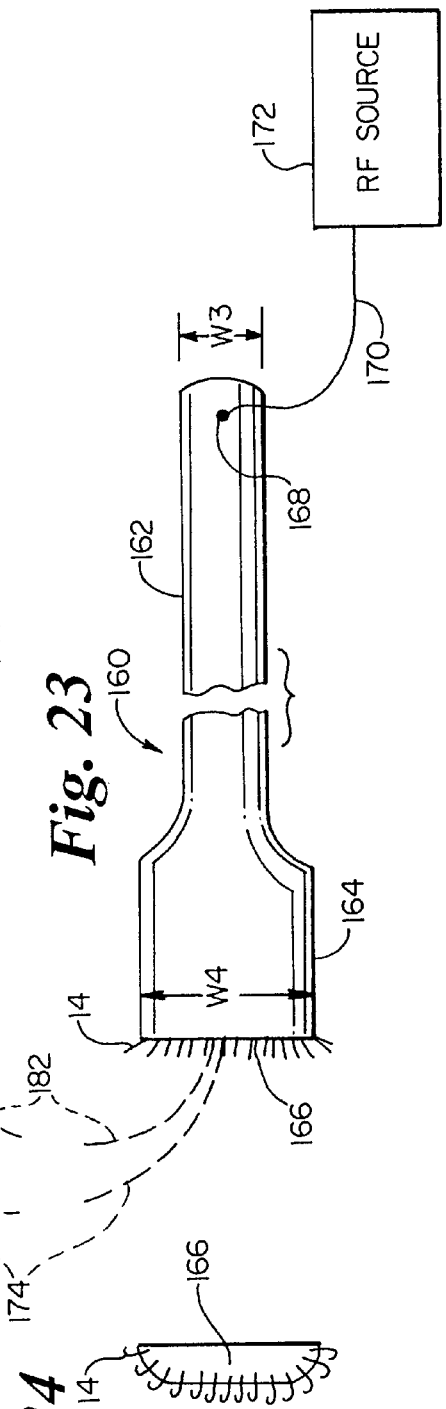
*Fig. 23*
*Fig. 24*

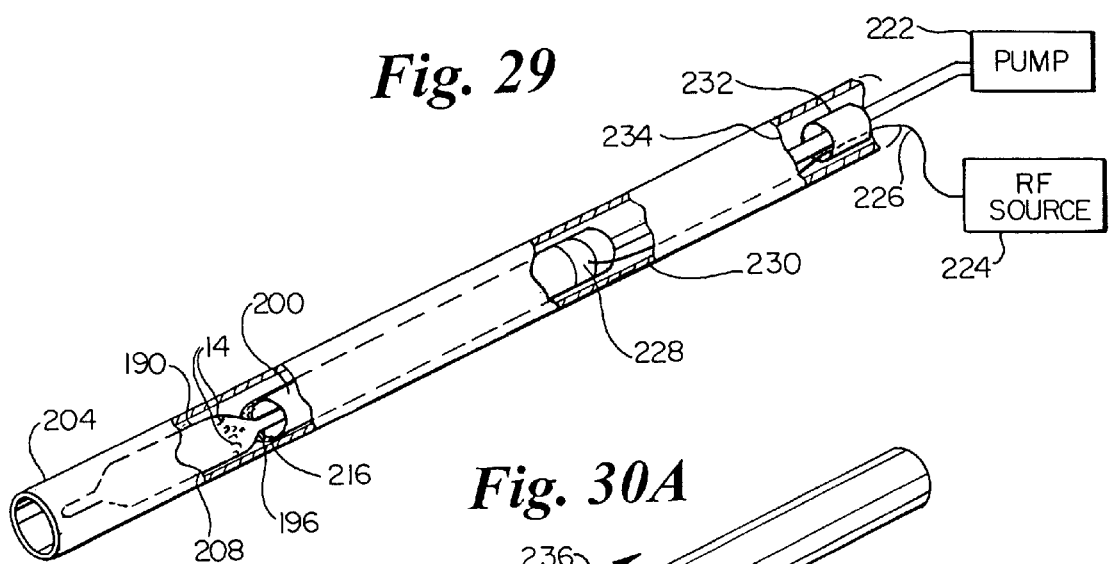
Fig. 29
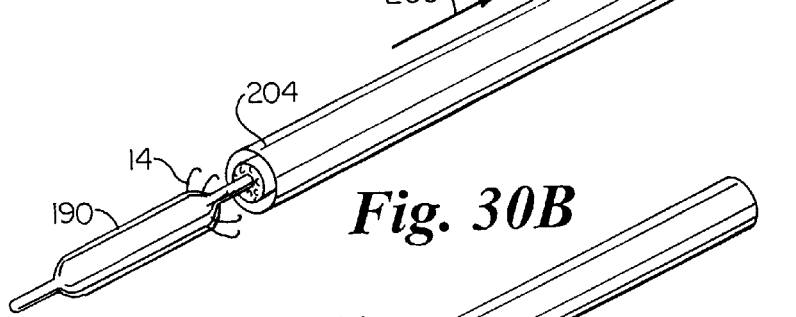
Fig. 30A
Fig. 30B
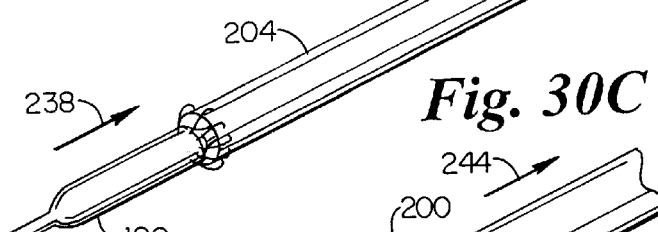
Fig. 30C
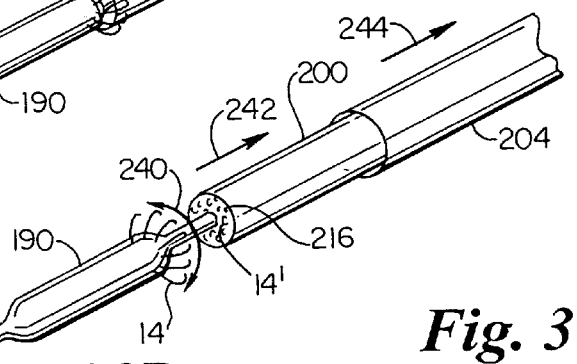
Fig. 30E
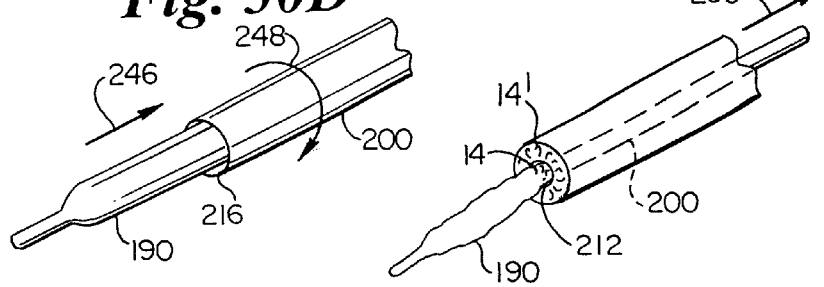
Fig. 30D

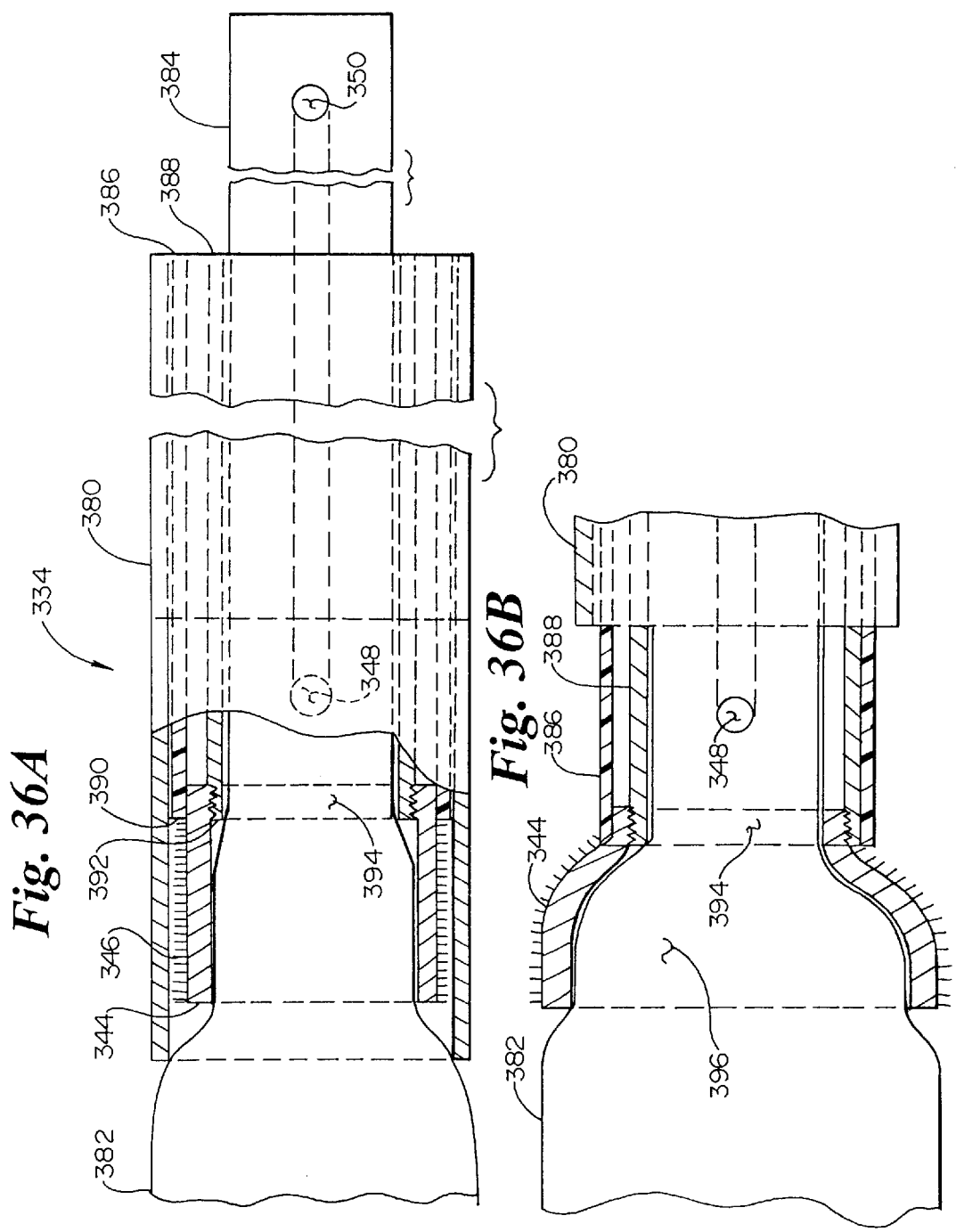

CLOSURE DEVICE AND METHOD

BACKGROUND OF THE INVENTION

1. Field of the Invention

The present invention relates generally to improved apparatus and methods for closing perforations in body organs or blood vessels, which are alternatives to suturing; and, more particularly, relates to closure apparatus having application for closure of openings in body organs or blood vessel walls after invasive procedures in a patient's system have been performed.

2. Description of the Prior Art

There are several surgical procedures where it is necessary to puncture a blood vessel or other body organs in order to insert a catheter or other structures therein. The punctures are utilized for a number of reasons including, but not limited to, diagnostic procedures, radiological procedures, application of medication or therapeutic devices, coronary and peripheral angioplasties, thorascopic, laparoscopic, or endoscopic surgery, and the like. These procedures all involve making a puncture in body organs or in the wall of a blood vessel to be treated or used in treatment of the patient's system. The size of the puncture will vary depending on the procedure. It is common to utilize the femoral artery as the point of entry to the patient's body in many such procedures.

One type of procedure involves percutaneous puncture of the wall of a blood vessel, such as an artery, by insertion of catheter through which a guidewire is inserted. When the guidewire is positioned, a treatment device such as an inflatable balloon, is advanced coaxially along the guidewire to the point of the treatment. Often a sheath (cannula) is advanced with the treatment device. The proximal end of the sheath is retained outside of the skin of the patient, and can be utilized with a hemostatic valve to prevent blood flow from the artery through the sheath.

Sheaths generally are flexible tubes having thin walls and diameters in the range of up to about 21 F or more. Other procedures, such as may be encountered with use of endoscopes or other instruments, may utilize trocars for insertion. Typical trocar punctures can range from 2 mm to more than 15 mm in diameter, or from about 6 F to more than 45 F. Closure is typically accomplished using multiple levels of sutures. Once a procedure is completed and the sheath or other instrument is to be removed, the resulting wound aperture can be significant. Frequently, after conventional diagnostic or treatment procedures, whether of the peripheral circulation or coronary circulation systems, excessive bleeding occurs upon removal of the catheter or arterial sheath. In addition to bleeding, hematoma formation can be significant in many post-interventional procedures.

While excessive bleeding can be a problem with persons having a normal blood clotting response, there are patients who are at even higher risk of excessive blood loss. These would include patients who are utilizing anticoagulation medications which inhibit clotting, suffer from obesity, hypertension, or bleeding disorders, all of which raise the risk of excessive bleeding following removal of the sheath or other instruments.

Various procedures and devices have been developed to address the minimization of blood loss upon completion of the diagnostic or treatment procedure. A common practice has been to simply apply pressure to the location of the perforation. Pressure may be required for a relatively long time, such as one-half hour, followed by the patient being substantially immobilized for many hours. This treatment essentially relies on the self-healing characteristics of the patient and relies on normal clotting. Pressure treatment can suffer, however, from the excessive loss of blood and thrombosis formation. Further, the development of hematoma can be a significant problem.

Another post-intervention process to close off the puncture aperture has been to apply a collagen plug. This procedure does not avoid all of the blood loss and the placement of such material adds to the risk of thrombosis formation and development of an inflammatory autoimmune reaction.

Various devices have been developed to close or repair punctures or perforation openings in a patient's body. One relatively straight forward method and apparatus for closing wounds is the use of clips. One form of hemostatic clip is shown in U.S. Pat. No. 4,217,902 to March et al., and requires sufficient accessibility of the wound to allow operation of a clamping mechanism. The self-attaching hemostatic clip has wound flap-engaging teeth for holding the flaps of the wound together when activated. This device does not, however, deal directly with closing an aperture in the wall of a vascular vessel and would allow the subcutaneous formation of thrombosis. Another type of clip is shown in U.S. Pat. No. 5,478,354 to Tovey et al., which describes a clip fastener that is placed over a wound with its legs embedded in tissue about the wound. This clip also requires an external tool for closing the clip legs, and when used externally, suffers from a similar concern of allowing blood to gather below the surface of the skin. An alternative embodiment involves surgical fasteners that are inserted through the wound and for attachment under the wound. These clipping devices present the potential problems involving the increase in thrombosis.

Another device for closing or connecting blood vessels is illustrated in U.S. Pat. No. 5,234,448 to Wholey et al., wherein a plurality of microminiature barbs mounted on a support member are utilized to pierce the wall of a blood vessel to anchor the device in place. In a related patent, U.S. Pat. No. 5,383,897 to Wholey, a similar patch utilizing a plurality of small barbs to adhere to the wall of the artery is described. When used internally to the blood vessel, it appears that such a patch arrangement can present a situs for clot formation.

Various suturing systems have been developed. For example, U.S. Pat. Nos. 5,304,184 to Hathaway et al.; 5,364,408 to Gordon; and 5,462,561 to Voda, illustrate various forms of suturing devices that can place suture material in a body cavity to join the tissue surrounding an opening or wound made during a medical procedure. The deep suturing procedures are relatively complex, require dexterity and care in placing the needles, and generally are time consuming in the completion of the suturing procedure. The amount of time required to complete the suturing function can result in substantial blood loss, especially when dealing with arterial punctures. There is the further concern of accuracy of placement of the suture needles to provide an adequate engagement of tissue such that the completed suture will hold. Finally, the introduction of a suture material within the blood vessel may support the formation of clots.

In procedures such as thorascopic, laparoscopic or endoscopic surgeries, it is common to make entry to the patient's body with a trocar of suitable size to form an aperture large enough to insert the applicable instrumentation. Closure of such incisions quickly and efficiently cannot be accomplished with prior art clamping or suturing processes or equipment.

SUMMARY OF THE INVENTION

With the state of prior art in mind, it is a primary objective of this invention to provide an improved closing device operable to close a puncture or opening in the wall of a blood vessel. In a preferred embodiment, the closing device includes support means with a distal end extending through the aperture to be closed, the support means having an engaging means mounted at the distal end, the engaging means arranged for engaging collagen fiber of adventitia as the support means and engaging means are withdrawn. The engaging means are atraumatic and slide past media, but become entangled in the collagen fiber in the adventitia, thereby allowing the support means to manipulate the tissue surrounding the opening in a manner such that it can be closed. The engaging means characteristically comprises a plurality of hooks that are of a size and orientation such that when moved outwardly from inside the blood vessel, the collagen fibers are engaged, and when the support means is twisted, the tissue flaps surrounding the aperture are drawn into proximity. With the puncture or opening thus closed, stasis can be achieved by leaving the device attached for a period of time by application of an adhesive (which may be a bioadhesive) or by applying localized heat to cauterize the tissue. The hooks are further positioned such that they can be backed out of hooking engagement with the adventitia for removal from the patient's body.

It is another object of the invention to occlude blood flow through an aperture in a blood vessel when closing the aperture.

In another embodiment, a distal inflatable balloon having a soft atraumatic distal tip and a proximal portion supporting a plurality of adventitia hooks can be positioned through the aperture in the blood vessel to occlude blood flow. When withdrawn, the hooks will engage the collagen fiber and allow it to be retracted. A closure probe having a distal end mounting a number of adventitia hooks is arranged for cooperation with the inflatable balloon. The closure probe includes radiofrequency (RF) windings for carrying radiofrequency signals to the vicinity of the aperture to be closed and can function to cauterize the closure tissue. When the inflatable balloon is inserted through a sheath and is exposed beyond the end of the sheath, the hooks on the proximal end can engage the adventitia from the inside of the vessel to be closed. When the balloon is withdrawn to contact with the distal tip of the closure probe, the closure probe and the hooks mounted at the distal end thereof can be twisted to engage the adventitia and hold the material fast. When thus held, the balloon can be prolapsed such that the adventitia hooks withdraw from the adventitia, and the balloon structure can be withdrawn through a lumen in the closure probe. When thus removed, the RF energy can be applied to cauterize and close the aperture in the wall of the blood vessel. Upon completion of the cauterizing, the closure probe can be reversed in rotation to remove the adventitia hooks and the structure removed from the body of the patient.

Still another object of the invention is to provide an improved closure device using a cauterizing device to complete closure of a puncture in a blood vessel.

In yet another embodiment of the invention, an elongated heating element has a plurality of hooks mounted at its distal end. When the heating probe is positioned through the aperture to be closed, the plurality of hooks are positioned such that when the probe is withdrawn, the hooks engage the adventitia. When the probe is rotated, the tissue surrounding the aperture is drawn closed, and the RF energy can be applied to cauterize the wound. The elongated probe can then be reversed in rotation such that the plurality of hooks disengage the adventitia, and the closing device can be withdrawn.

Yet another object of the invention is to provide an improved closing device with an improved method of guiding cauterizing probes to the puncture wound to be closed.

In another embodiment of a closing device of the present invention, a guide mechanism is adapted for positioning the closing device in proximity with the opening to be closed. At least one channel is provided in the guide mechanism along which an electrode can be passed to the point beyond the opening to be closed. The electrode includes a plurality of hooks at its distal end that are arranged to pass along the associated channel and be exposed when extended past the distal tip of the positioning device. When thus positioned, the positioning mechanism can be withdrawn, the electrode twisted and retracted to engage the adventitia, and the RF energy applied to close the wound. In an alternative arrangement, the positioning probe can include a pair of opposed channels for accommodating a pair of electrodes. In yet another aspect of this embodiment, the positioning member can include a longitudinal lumen having a distal opening at the distal tip of the positioning mechanism and a proximal opening at a position outside the patient's body. This lumen can be utilized to monitor positioning of the closing device within the blood vessel of the vascular system, wherein blood will flow through the lumen to the proximal opening. When properly positioned and the one or more electrodes are positioned to engage the adventitia, the blood flow can be monitored during closure of the aperture in the wall of the blood vessel.

Still a further object of the invention is to provide a closing device that can temporarily occlude blood flow and utilizes blood flow to monitor location of the closing device.

In still another embodiment of the inventive closing device, a collapsing occluder having a distal atraumatic tip and a plurality of proximal blood vent holes is arranged for cooperation with a plurality of adventitia hooks deployable in proximity to the blood vent holes. The blood vent holes cooperate with an internal lumen, and are used for detecting positioning of the closing device through the hole in the blood vessel wall that is to be closed. Upon engagement of the plurality of hooks in the adventitia from the inside of the blood vessel, the occluder is collapsed and withdrawn from the patient's body. When the hooks are rotated, the aperture is closed. The wound can be closed by application of RF energy or hydro-softening hooks can be left in place.

Another object of the invention is to provide an improved closing device that hooks the adventitia to close an aperture and clamps the aperture closed.

In another embodiment of the improved closing device, a plurality of hooks are deployed to the inside of a blood vessel through a sheath such as the type used for angioplasty, and are utilized to engage the collagen fiber in the adventitia from the inside of the blood vessel. When thus engaged, the plurality of hooks hold the adventitia and an annular closure ring can slide down over the hooks to form an interlocking connection with the hooks and thereby hold the blood vessel material firmly closed. The hooks can be disengaged from the support and delivery mechanism, and left in place. When the closing device comprising the plurality of hooks and the annular locking ring are constructed of bio-absorbable material, the opening in the blood vessel can be quickly closed, the closing device left in place, and the patient minimally impacted.

Still a further object of the invention is to provide a closing device that utilizes a hook and pile bio-absorbable fabric.

In another embodiment of the invention, an elastic fabric ring has outer hooks for engaging the adventitia in the wound to be closed and an inner hook and pile structure for holding the wound closed. The closing device can be deployed through a sheath and, when properly positioned, exposed and expanded to engage the adventitia. After proper positioning and expansion, the closure device is twisted to cause engagement of the outer hooks with the adventitia and closure of the wound. When thus engaged and twisted, the deployment mechanism is withdrawn, the closure device contracts such that the inner hook and pile members engage and hold the closure device in place. Additionally, suture material can be affixed to the closure device to allow the closure ring to be drawn together to thereby bring the inner hook and pile material into tighter contact with itself to engage the holding action. Preferably, the closing device of the embodiment is constructed from bio-absorbable material, thereby allowing the opening to be quickly closed, and the closing to be left in place.

These and other more detailed and specific objectives and an understanding of the various embodiments of the invention will become apparent from a consideration of the following Detailed Description of the Preferred Embodiments in the view of the drawings.

BRIEF DESCRIPTION OF THE DRAWINGS

FIG. 1 is side view of the distal end of the closing device of this invention;

FIG. 2 is an end view of the closing device shown in FIG. 1;

FIG. 3A is a side view of an adventitia hook;

FIG. 3B is a face view of the hook shown in FIG. 3A;

FIG. 4A is a side view of an alternative embodiment of an adventitia hook;

FIG. 4B is a face view of the hook shown in FIG. 4A;

FIG. 5A is a schematic, partially sectioned view showing an arterial sheath, the adventitia to be used in closing an aperture in an artery wall, and a closing device being positioned;

FIG. 5B is a schematic, partially sectioned view of a closing device deployed within the aperture;

FIG. 5C is a schematic, partially sectioned view of a closing device passing through the media to engage adventitia;

FIG. 7 is a schematic view of an embodiment of a closing device and a closure locking ring;

FIG. 8A and FIG. 8B illustrate different configurations of hook mounting and deployment;

FIG. 9 is a side view of a hook having a plurality of raised ridges along the inner leg surface;

FIG. 10 is a face view of an embodiment of an annular closure locking ring;

FIG. 11 is a cross-sectional view taken at line 11—11 in FIG. 10;

FIG. 12A is a side view of an alternative embodiment of a hook having a barb at its hooking end and a plurality of raised ridges along the inner leg surface;

FIG. 12B is a top view of the hook shown in FIG. 12A;

FIG. 13 is a face view of an alternative embodiment of an annular closing locking ring;

FIG. 14 is a cross-sectional view taken at line 14—14 in FIG. 13;

FIG. 15 is a schematic diagram illustrating placement and interaction of a closing device utilizing a plurality of biased hooks and an annular closure locking ring;

FIG. 16 is a section view of a plurality of adventitia hooks and an annular closure locking ring closing an aperture in the wall of a cardiovascular member;

FIG. 21 is a partial schematic diagram of another embodiment of a placement system for placing cauterizing probes in vicinity of an aperture to be closed, and includes a blood-flow monitoring system;

FIG. 22 is a tip view of the placement system of FIG. 21;

FIG. 23 is a top view of a cauterizing electrode to be used in conjunction with the placement system of FIG. 21;

FIG. 24 is an end view of the electrode shown in FIG. 23;

FIG. 29 is a partial schematic diagram of a closing device utilizing the balloon occluder shown in FIG. 25 and the closure probe shown in FIG. 27, encased within a sheath for placement, and with portions broken away;

FIG. 30A through FIG. 30E are a sequence of partial schematic diagrams that illustrate the interaction of components and the method of closing an aperture utilizing the closing device shown in FIG. 29;

FIG. 36A is a partial cross-sectioned schematic diagram of the embodiment of the closing device of FIG. 34A illustrating the relationship of the elastic closure ring and the positioning system during the initial positioning process;

FIG. 36B is a partial cross-sectional schematic diagram of the closing device shown in FIG. 36A with the elastic closure ring being deployed to an adventitia engaging position;

DETAILED DESCRIPTION OF THE PREFERRED EMBODIMENTS

Figure 6A:
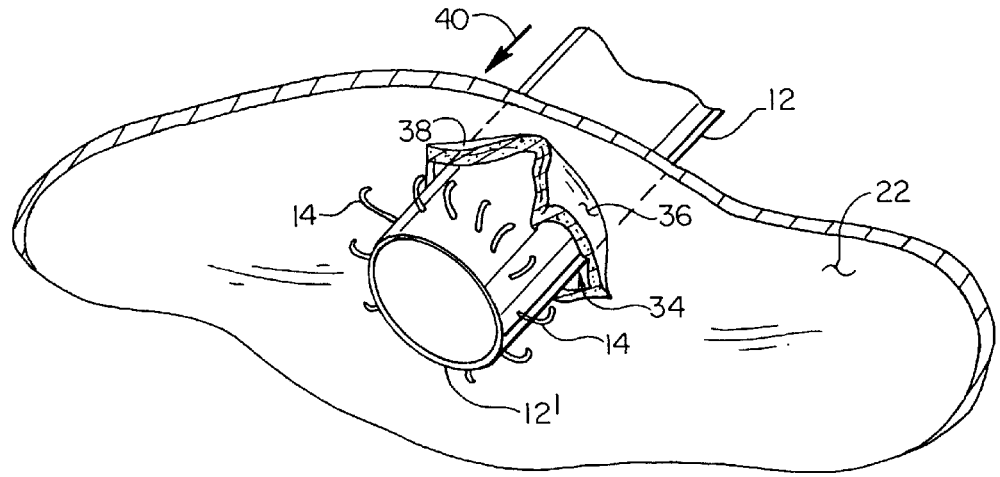
FIG. 6A is a partial perspective view of the distal end of a closing device extending through an aperture to be closed.

FIG. 1 is a side view of the distal end of the closing device of this invention. The closing device 10 has a longitudinal support member 12 with a distal tip 12'. A plurality of hooks 14 are radially mounted in proximity to distal tip 12. In one configuration, hooks 14 are aligned with their hooking elements parallel to centerline 16. In another configuration, hooks 14 can be oriented offset from centerline 16 as shown by dashed hook 14'. The number and configuration of the plurality of hooks 14 will depend upon the materials selected for the hooks and the particular embodiment of the invention.

Closing device 10 will vary in dimension according to the size of the aperture or puncture in a patient's body organs or in a blood vessel wall that is to be closed. In arterial closures, the punctures developed in angioplasty procedures and the like can be relatively large. The closure device is developed such that it can be deployed through the wound in the patient's body through a sheath represented by dashed lines 18, which characteristically will extend from outside the patient's body with it's distal end within the lumen of the blood vessel through the aperture to be closed.

The support member 12 can be up to 8 F guide tube or larger, and hooks 14 can have a cross sectional diameter in the order of 0.018 inch. The hook structural size depends upon the material composition of hooks 14 and the method of attachment to support member 12.

The hooks 14 are illustrated as rather large devices. Depending on the application, the hooks 14 can have cross-sectional dimensions ranging from millimeters to micromillimeters. The solution of size will depend on the target closure site and the size of the aperture to be closed. Though shown in the illustrations as actual hook elements, it should be understood that any structure that will engage the adventitia fibers will allow the closure action. For example, the hooks 14 could be adventitia hooking fibers having snagging characteristics. Such snagging characteristics can be achieved with barbs or in some applications, by a snagging surface finish.

FIG. 2 is an end view of the closing device shown in FIG. 1. As shown, there are eight hooks 14 mounted near distal tip 12', and this configuration has been found to be adequate in many circumstances. It should be understood, however, that more or fewer hooks can be utilized depending upon the embodiment and organization of the closing device.

FIG. 3A is a side view of an adventitia hook 14 having a shank portion 14-1 and a hook portion 14-2. The adventitia hooks are designed to be atraumatic and to slide past media in the wall of the blood vessel in which an aperture is to be closed. The media tissue layer is smooth and not fibrous. The hooks are designed and intended to engage the collagen fibers of the adventitia when pulled through the aperture from inside the lumen of the blood vessel to be closed toward the outside. The closure device can be utilized with any tissue having adequate fiber to allow engagement of the hooks.

FIG. 3B is a face view of the hook shown in FIG. 3A. This hook 14 has the hook portion 14-2 in alignment with the shank portion 14-1. This configuration provides a direct engagement when withdrawn, and allows the hook to remain engaged when support member 12 is rotated either clockwise or counterclockwise.

FIG. 4A is a side view of an alternative embodiment of an adventitia hook. Hook 14A has a shank portion 14A-1 and hook portion 14A-2. FIG. 4B is a face view of the hook shown in FIG. 4A. In this configuration, the hook portion 14A-2 is offset from the alignment of shank 14A-1, somewhat in the configuration of a fish hook. This configuration can provide additional hooking capability when the support member 12 is rotated.

Hooks 14 can be constructed of various materials, with the material selection depending upon the particular embodiment of the closure device. The hooks 14 can be rigid or flexible depending on the application. For the embodiment shown in FIG. 1, it has been found advantageous to have hooks 14 constructed of plastic material and may be a material such as marketed under the trademark Velcro®. Other plastics or flexible materials, either removable or bio-absorbable can allow hooks 14 to be deflected out of hooking alignment within sheath 18 during deployment. This deflected deployment allows a smaller sheath and allows the distal tip 12' to be positioned through the aperture to be closed into the lumen of the blood vessel. When the closing device 10 is then exposed by withdrawal of sheath 18, hooks 14 project and are in position to engage the collagen fiber when brought in contact therewith. Other hook materials will be described below.

FIG. 5A is a schematic, partially sectioned view showing an arterial sheath, the adventitia to be used in closing an aperture in an artery wall and a closing device being positioned. In this illustration, an artery is the blood vessel to be closed, the artery having a arterial sheath 20 and adventitia 22 and a media 24. Sheath 18 is moved in the direction of arrow 26 until its distal tip 18' extends below the media 24. When thus positioned, support member 12 is moved in the direction of arrow 28 to move hooks 14 through the lumen of sheath 18. As illustrated, hooks 14 are deflected within sheath 18.

FIG. 5B is a schematic, partially sectioned view of a closing device deployed within the aperture. The distal tip 12' of support member 12 has been extended beyond the distal tip 18' of sheath 18. Hooks 14 are shown deployed and in position to form the closure operation.

FIG. 5C is a schematic, partially sectioned view of a closing device passing through the media to engage adventitia. When the sheath is moved in the direction of arrow 30 and the closing device is moved in the direction of arrow 32, hooks 14 pass through the media 24 without engagement, and continue until the hooks 14 engage the collagen fiber in adventitia 22. When hooks 14 have engaged adventitia 22, support member 12 is rotated in either direction, as shown by arrow 34 sufficiently to cause adventitia 22 to be drawn into a wrapped closure. It is of course understood that when hooks 14 are deployed to enhance hooking in one direction, the removal is accomplished by rotation in the reverse direction. Depending upon the aperture to be closed, the nature of the blood vessel being treated, and the structure of the closing device, it has been found that usually less than one complete revolution will be sufficient to close the aperture. It is not uncommon for one-quarter to one-half turn to be sufficient to form the closure.

FIG. 6A is a partial, perspective view of the distal end of a closing device extending through an aperture to be closed. The shape of aperture 34 will depend upon the nature of the instrument causing the perforation. It is quite common for a trocar and associated cannula (not shown) to cause an aperture 34 to have a generally Y shape, for example having flaps such as flaps 36 and 38. Support member 12 is shown passing through aperture 34 in the direction of arrow 40 with distal tip 12' and hooks 14 within the lumen of the blood vessel being treated and beyond the inner layer of adventitia 22. For descriptive purposes, sheath 18 has not been shown, but it would be understood to have been in place during the deployment of support member 12.

Figure 6B:
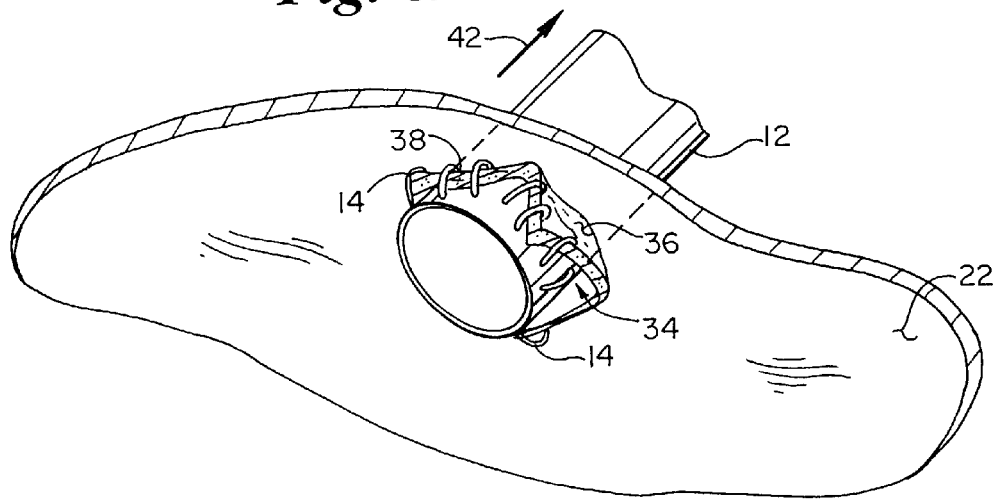
FIG. 6B is a partial perspective view of the distal end of a closing device engaging the adventitia adjacent an aperture to be closed.

FIG. 6B is a partial, perspective view of the distal end of a closing device engaging the adventitia adjacent an aperture to be closed. As illustrated, support member 12 has been moved in the direction of arrow 42 such that hooks 14 have engaged the flaps 36 and 38 of aperture 34, and are in position to complete the closure.

Figure 6C:
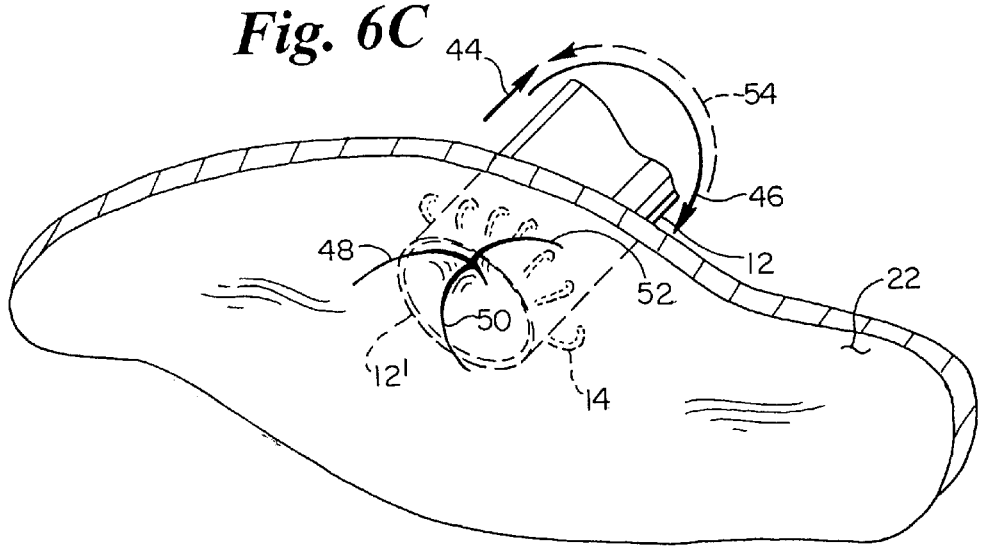
FIG. 6C is a partial perspective view illustrating the closing action of a closing device.

FIG. 6C is a partial perspective view illustrating the closing action of a closing device. When support member 12 has been moved sufficiently in the direction of arrow 44, support member 12 can be rotated in the direction of arrow 46 thereby drawing flaps of aperture 34 into a folded over closure illustrated by closure lines 48, 50 and 52. This closure configuration is, of course, illustrative only, and more or fewer overlaps may result. When aperture 34 is closed, blood flow is inhibited, and the closure can be completed. Closure can occur through the self-healing process or clotting, by holding the closure device in place until such clotting occurs. Alternatively, closure can be accelerated by cauterizing, as will described in more detail below, or by implantation of a interlocking closure device that can be left in place, again as will be described in more detail below. Once the closure has been completed and the closing device is to be removed, it can be counter rotated in the direction of dashed arrow 54 to disengage hooks 14 from the collagen fiber for removal.

FIG. 7 is a schematic view of an embodiment of a closing device and a closure locking ring. In this configuration, closing device 10 is comprised of support member 12 having a distal end 12', a plurality of hooks 14, and an annular closure locking ring 60 slidably engaged with support member 12. Closing device 10 is deployed within sheath 18, sliding mechanism 62 is used to engage annular closure locking ring 60 to thereby move it into locking contact with hooks 14. Trapped adventitia is thereby held in place. In this configuration, hooks 14 are disengaged from support member 12 and left within the closing device.

FIG. 8A and FIG. 8B illustrate different configurations of hook mounting and deployment. In FIG. 8A, there are eight hooks 14 shown mounted in the vicinity of distal tip 12'. Hooks 14 can be comprised of bio-absorbable material and can be glued to the surface of support member 12 using a glue that softens and releases when moistened. FIG. 8B illustrates a larger number of hooks 14 and can be similiarly constructed.

FIG. 9 is a side view of a hook having a plurality of raised ridges along the inner leg surface. Hook 14 has a shank portion 14B-1 and an atraumatic hook portion 14B-2. A plurality of ridges 14B-3 are arranged along the inner surface 14B-4 of shank 14B-1. These ridges 14B-3 are positioned to cooperate with an inner surface (to be described in more detail below) of a portion of the annular closure locking ring 60.

FIG. 10 is a face view of an embodiment of an annular closure locking ring. Annular ring 60 has an inner member 66 defining an inner annular aperture 68, and having an inner annular surface 70. An outer surface 72 supports a cup-like member 74. The arrangement is such that when the shanks of hooks 14 are drawn within annular aperture 68, the shanks form a friction fit with inner surface 70, thereby locking the closing device with adventitia held by the hooks within cup member 74.

FIG. 11 is a cross-sectional view taken at line 11—11 in FIG. 10. This illustrates in cross-section the mounting of cup member 74 and the configuration of annular aperture 68.

FIG. 12A is a side view of an alternative embodiment of a hook having a barb at its hooking end and a plurality of raised ridges along the inner leg surface. Hook 14C has a shank 14C-1 with a hook barbed point 14C-2. A plurality of raised reverse ridges 14C-3 are formed on the inner surface 14C-4.

FIG. 12B is a top view of the hook shown in FIG. 12A. This illustrates the offset of barbed hook end 14C-2 and the positioning of reverse ridges 14C-3.

FIG. 13 is a face view of an alternative embodiment of an annular closure locking ring 60A. The annular inner member 66A has a plurality of raised ridges 76 on inner surface 70A.

FIG. 14 is a cross-sectional view taken at line 14—14 in FIG. 13. The plurality of annular ridges 76 are configured on inner surface 70A and are oriented with a reverse slant of the raised ridges 14B-3 or 14C-3 of the associated hook structures. This configuration operates to cause the annular ridges 76 to engage a plurality of shanks and hold them in place within the circular aperture 68A.

FIG. 15 is a schematic diagram illustrating placement and interaction of a closing device utilizing a plurality of biased hooks and an annular closure locking ring. This configuration is a modification of the structure illustrated in FIG. 7. It differs primarily in the mounting of the hook structures. Support member 12 at its distal end 12' supports a plurality of outwardly biased leg members 80, each of which has a distal end 82 to which a respectively associated hook 14B is removably affixed. The outward bias of legs 82 is restrained within sheath 18 such that they are positioned with sheath 18 as illustrated by dashed member 82' with its associated hook 14B'. Sheath 18 can have a widened entry portion 18-1 to allow the outwardly biased hook members 82 to be brought into confinement within sheath 18 when entered in the direction of arrow 84. The plurality of hooks are retained within sheath 18 until the sheath is positioned within the aperture in the wall of the blood vessel that is to be closed. Annular closure locking ring 60 is slidably engaged on support member 12.

When the closing device is enclosed within sheath 18, the entire assembly is moved in the direction of arrow 86 into selected position such that the distal end 18-2 of the sheath is within the lumen of the blood vessel to be closed. When thus positioned, a holding force is applied to hold support member 12 in place and the sheath is partially withdrawn in the direction of arrow 88, such that the distal tip 18-2' allows the spring biased legs 80 to extend the hooks 14B outwardly into an adventitia engaging position. When thus exposed, support member 12 is moved in the direction of arrow 90 causing the plurality of hooks 14B to engage the collagen fibers in the adventitia. Once so engaged, support member 12 is held firmly in place, and the slidable member 60 is moved in the direction of arrow 92 to impart motion to the annular closure locking ring 60, thereby causing it to move in the direction of arrow 94. When moved into a locking position, as will be described in more detail below, the shanks of hooks 14B are retained within the annular closure locking ring 60 with the connection points 82 extending through and proximal annular ring 68. The configuration of the hooks 14B could be any of the other embodiments of hook structures described above. Similarly, the annular closure locking ring 60 could also be the configuration illustrated in FIG. 13 and FIG. 14. In the preferred configuration, hooks 14B and the annular closure locking ring 60 are constructed of bio-absorbable plastic which will dissolve when left in the patient's body. Characteristically such dissolving action may occur in one to two months. A preferred method of attaching the hooks 14B to the outwardly biased members 80 is through attachment with bio-glue. Characteristically bio-glue will dissolve in 4–6 hours and is available commercially.

It has been recognized that other apparatus or methods of releasing the hooks 14B can be utilized. A first option other than the use of a dissolving glue is to deploy a cutter tool (not shown) within sheath 18 to a position above locking ring 60 to thereby cut the hooks 14B loose. Another option (not illustrated), is to utilize the structure in conjunction with an RF cauterizing probe wherein the heat will cause the hooks 14B to be released. Yet another option (not illustrated) is to utilize an ejector within support member 12 to mechanically eject the hooks 14B when activated. The preferred separation mechanism is the dissolving glue in that it results in a minimum mechanical disturbance to the wound closure.

FIG. 16 is a section view of a plurality of adventitia hooks and an annular closure locking ring closing an aperture in the wall of a cardiovascular member. This illustrates the plurality of hooks 14B engaging the adventitia 22 with the annular closure locking ring 60A bearing down on the facia 20 and holding the adventitia 22 firm against hooks 14B. The ridges on the shank of hooks 14B are interlocked with the reverse angled ridges 76 on the inner surface 70A of the annular ring. When the closure is completed, the sheath 18 and the support member 12 with the actuating member 62 are removed from the patient's body leaving the locked closing device in place.

Another embodiment of the invention utilizes adventitia engaging hooks in combination with cauterizing elements.

Figure 17:
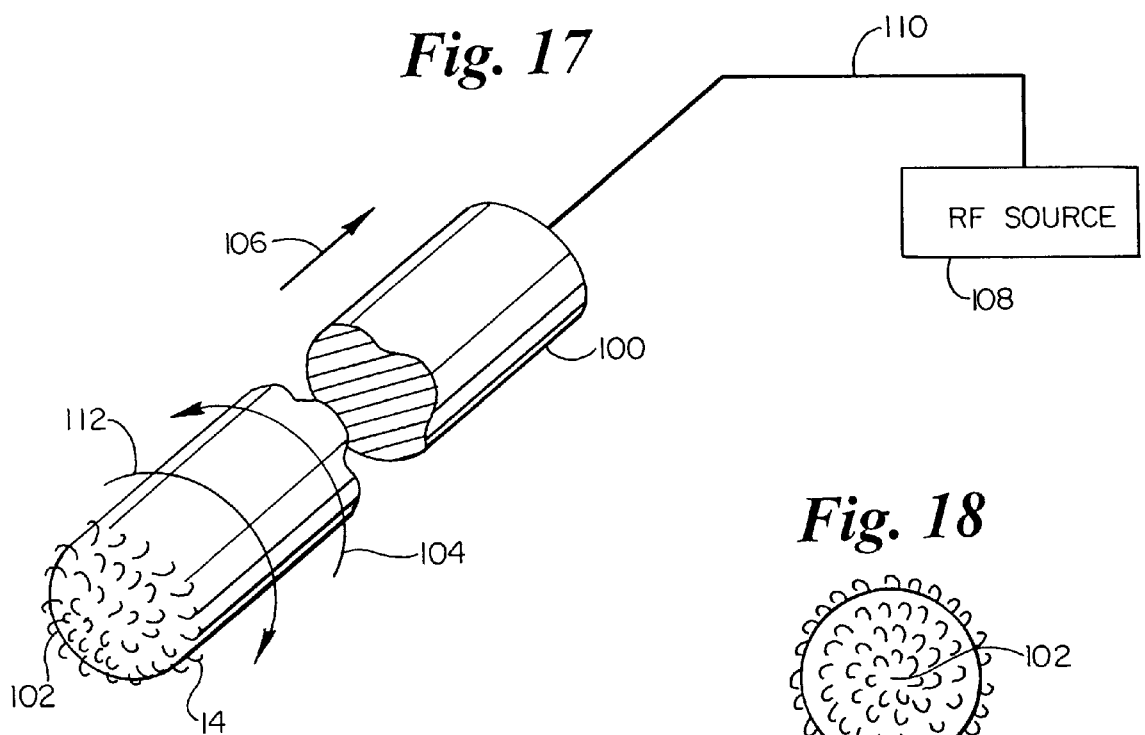
FIG. 17 is a schematic diagram of an alternative embodiment of a closing device having a plurality of adventitia hooks mounted to the tip of a cauterizing probe.

FIG. 17 is a schematic diagram of an alternative embodiment of a closing device having a plurality of adventitia hooks mounted at the tip of a cauterizing probe. A cauterizing probe 100 is of a type available commercially and has a plurality of adventitia engaging hooks 14 mounted at its distal tip 102. The distal tip 102 is characteristically rounded and the hooks 14 are mounted in a configuration to provide a hooking action when the probe 100 is rotated in a first direction. The probe 100 can be positioned through a sheath (not shown) with the hooks 14 covered during the positioning process. This allows the tip 102 to be placed through the aperture in the blood vessel wall that is to be closed. When thus positioned, the sheath can be withdrawn and the probe 100 rotated in a first hooking direction such as indicated by arrow 104 while exerting withdrawal pressure as indicated by arrow 106. This hooking and twisting action will cause the puncture to be closed as described above. When thus closed, RF power can be provided from an RF source 108 via wire 110 thereby causing the probe 100 to cauterize and close the puncture. Controlled RF sources are known and are available commercially. When the cauterizing closure has been accomplished, the probe 100 can be reverse rotated as indicated by arrow 112, to thereby cause the hooks 14 to disengage and to allow removal of the probe from the body of the patient.

Figure 18:
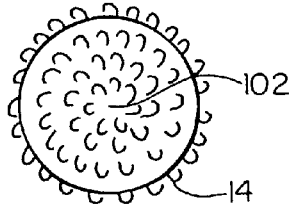
FIG. 18 is a tip view of the closing device of FIG. 17.

FIG. 18 is tip view of the closing device of FIG. 17. It illustrates the configuration of hooks 14 on distal tip 102.

Figure 19:
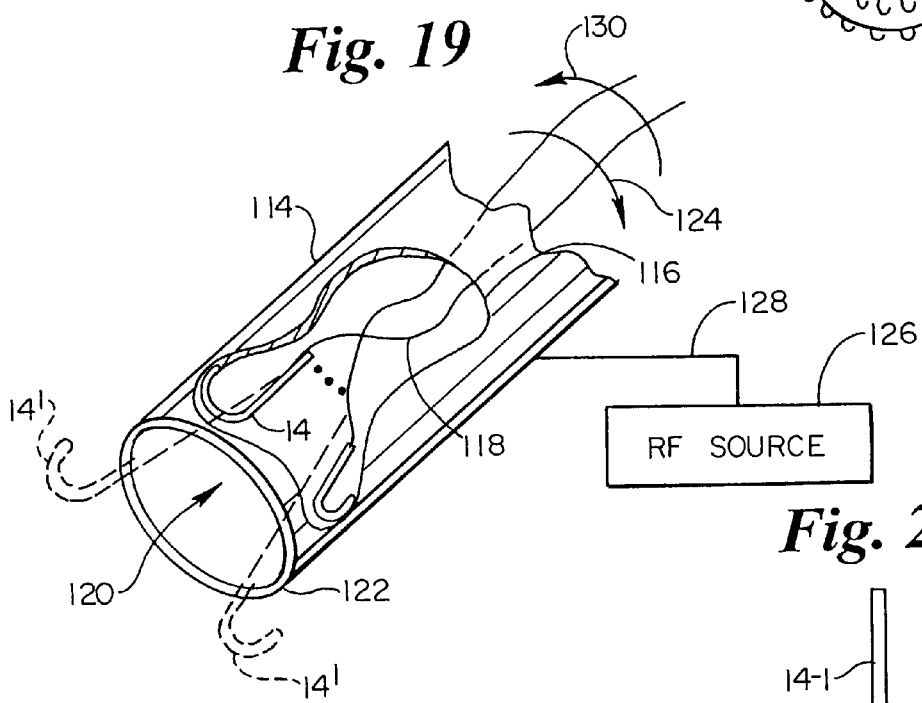
FIG. 19 is a partial schematic diagram of another embodiment of a closing device having a plurality of outwardly biased adventitia hooks that can be deployed from within the lumen of a cauterizing probe.

FIG. 19 is a partial schematic diagram of another embodiment of the closing device having a plurality of outwardly biased adventitia hooks that can be deployed from within the lumen of cauterizing probe. In this configuration, a cauterizing probe 114 has a broken away portion 116 that illustrates hooks 14 restrained therein with outwardly biasing mounting members 118. In this configuration, the hooks 14 are retained within the lumen 120 of the cauterizing probe during positioning. Once the distal tip 122 of probe 114 is through the aperture in the vessel wall to be closed, the plurality of hooks 14 can be urged outwardly in a manner such that the hooks 14' shown in the dashed position are in a position capable of engaging the adventitia when withdrawn. Once the hooks engage the adventitia, the support structure 118 can be moved in the direction of arrow 124 to cause closure of the blood vessel wall puncture that is being closed. When thus closed, an RF source 126 applies RF energy via wire 128 to cause the probe 114 to cauterize the wound and close it. Again, rotation of the support members 118 in a reverse direction such as indicated by arrow 130 will cause the hooks to disengage and allow removal of the closing device from the body of the patient.

Figure 20:
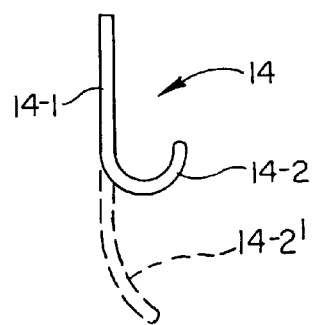
FIG. 20 illustrates another embodiment of a hook whose shape changes when heated.

FIG. 20 illustrates another embodiment of a hook whose shape changes when heated. It has been found to be advantageous to utilize adventitia hooks 14 that change structural configuration upon application of heat. The material Nitinol can be formed in a configuration such that the shank 14-1 has a hooking element 14-2 when the hook 14 is at a normal working temperature that can be in the order of about 38°C. The Nitinol material has a characteristic that when heated, it will tend to straighten from its material-memory position, as indicated by dashed member 14-2, upon application of heat. The straightening action can occur with the elevation of temperature to the order of about 50°C. This releasing action of hook 14 finds particular advantageous usage in conjunction with cauterizing probes and aids in the removal of the closing device from the patient's body.

FIG. 21 is a partial schematic diagram of another embodiment of a placement system for placing cauterizing probes in the vicinity of an aperture to be closed, and includes a blood-flow monitoring system. The placement system 140 has a distal end 142 and a proximal end 144. A broken away section 146 illustrates a blood-flow lumen 148 that extends from an opening 150 in the distal tip 142 throughout the length of the placement system to a flow port 152. The blood-flow lumen is utilized in positioning the placement system 140 through the aperture or puncture wound to be closed, and into the blood flow system. When blood flows through lumen 148, it can be observed exiting from port 152, and indicates that distal port 150 is within the lumen of the blood vessel. During positioning, blood will not normally flow through lumen 148, thereby indicating that the placement system is not appropriately positioned through the aperture that is to be closed. A pair of longitudinal channels 154 and 156 extend along the length of the placement system 140, and are utilized to guide associated cauterizing electrodes to an appropriate position through the aperture within the lumen of the blood vessel wall that is to be closed.

FIG. 22 is a tip view of the placement system of FIG. 21. It can be seen that channels 154 and 156 are open upwardly and downwardly, respectively. The channel opening W1 is a dimension less than the bottom of the channel W2. The shape of channels 154 and 156 approximate the shape of associated cauterizing probes, and are of a shape to slidably retain the cauterization probes during positioning, as will be described in more detail below.

FIG. 23 is a top view of a cauterizing electrode to be used in conjunction with the placement system of FIG. 21. The cauterizing electrode 160 has a proximal portion 162 having a width W3 that will slide within the opening of channel 154 and is less than width W1. The distal head portion 164 of cauterizing probe 160 has a plurality of hooks 14 mounted at the distal end 166. The width W4 of head 164 is less than the width W2 of channels 154 and 156.

FIG. 24 is an end view of the electrode shown in FIG. 23. The plurality of hooks 14 are mounted in a predetermined hooking configuration at distal end 166. Hooks 14 can be selected from any of the hook structures described above, and the probes 160 are affixed with an electrical interconnection point 168 that allow interconnection via wire 170 to an Rf source 172.

In operation, an RF probe 160 can positioned in the direction of dashed arrow 174 into channel 154. This is accomplished as shown in the dashed line representation of probe 160 with the distal tip 166 being slid down sloping portion 176 into the proximal channel opening 178. This is accomplished by causing head portion 164 to enter channel 154 as probe element 162 is moved downwardly and forwardly as shown by dashed arrow 180. When the head member 164 is positioned within channel 154, it can be moved along the length of channel 154 until it extends past the distal tip 150. A similar action can be utilized by moving a second probe 160 in the direction of dashed arrow 182 for movement to the point of the wound to be closed at the distal end of channel 156.

When the probe or probes are moved through and beyond channels 154 and 156, the hooks 14 are exposed for engaging the adventitia in the vicinity of the aperture to be closed. At that time, the head 164 of probe 160 is released from the associated channel, and may be manipulated to cause engagement with the adventitia. Once the probes are engaged with the adventitia, the placement system 140 can be withdrawn, and there will be an indication of no blood flow if the aperture is properly closed. When thus closed, the RF source 172 can be activated to apply the RF power over wire 170. Only one cauterizing electrode 160 is shown, and it should be understood that they can be used in pairs as described.

In some applications it has been found to be advantageous to inhibit or occlude blood flow during the closure of a puncture in the wall of the blood vessel.

Figure 25:
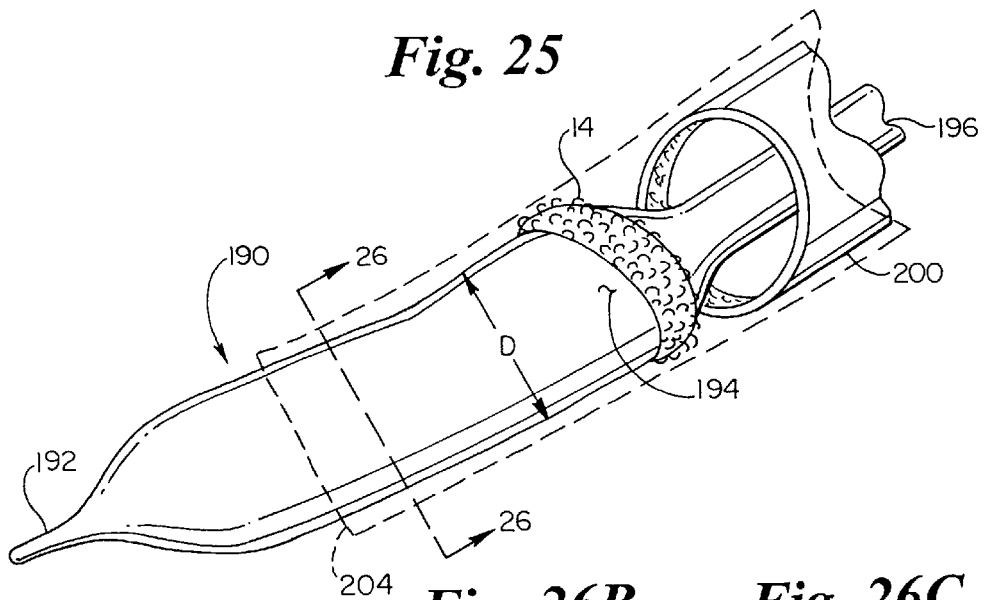
FIG. 25 is a schematic diagram of an inflatable balloon occluder to be used in closing an aperture in a wall of a blood vessel, and illustrates a plurality of hooks at the proximal end of the occluder.

FIG. 25 is a schematic diagram of an inflatable balloon occluder to be used in closing an aperture in a wall of a blood vessel, and illustrates a plurality of hooks at the proximal end of the occluder. The inflatable balloon occluder 190 has a soft atraumatic distal tip 192 and a plurality of adventitia engaging hooks 14 mounted at the proximal end 194. Tube 196 passes out of the patient's body and is used to control the inflation and deflation of inflatable balloon occluder 190, as will be described in more detail below. The inflatable balloon occluder 190 is normally deployed through an associated outer sheath, (not shown in detail), for example of the type used in angioplasty procedures. The maximum outside diameter of the occluder will be selected to fit within the outer sheath during deployment, and illustratively may be in order of up to about 8 F or more. The diameter will of course to be selected to accommodate the diameter of the lumen of the blood vessel to be treated. The balloon 190 operates in conjunction with an RF wound closure probe 200, as will be described in more detail below. The total structure can include a proximal blood seal (not shown) for monitoring flow of blood through the lumen of the RF wound closure probe 200, and can be used in placement of the closing device and monitoring whether blood flow occlusion has actually occurred. Inflatable balloon occluders are known, and can be of the foam core or roll core variety. Though not shown in detail, a sheath is represented by dashed line 204.

Figure 26A:
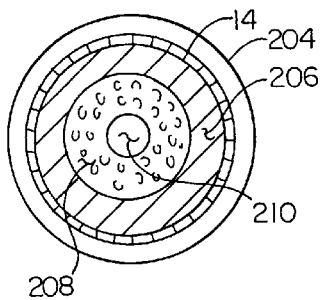
FIG. 26A is a cross-sectional view taken at line 26—26 in FIG. 25 when the balloon occluder has an air foam core.

FIG. 26A is a cross-sectional view taken at line 26—26 in FIG. 25 when the balloon occluder has an air foam core. As shown, sheath 204 surrounds the plurality of hooks 14. The wall 206 of the balloon occluder encapsulates the air foam material 208 with air being injected or removed through aperture 210 within member 196.

Figure 26B:
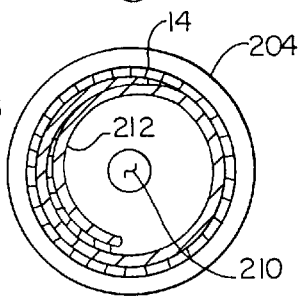
FIG. 26B is a cross-sectional view taken at line 26—26 in FIG. 25 when the balloon occluder has a roll core.

FIG. 26B is a cross-sectional view taken at line 26—26 in FIG. 25 when the balloon occluder has a roll core. Again, sheath 204 surrounds a plurality of hooks 14 mounted to the surface of roll core balloon member 212. When air is introduced into the balloon occluder 190 through aperture 210, the roll core member 212 is caused to move outwardly forming the expanded balloon occluder. When air is withdrawn, the roll core collapses and the overall diameter of the inflatable balloon occluder 190 is reduced.

Figure 26C:
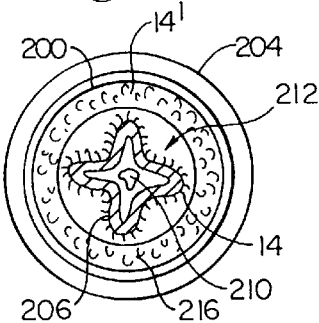
FIG. 26C is a cross-sectional view taken at line 26—26 in FIG. 25 when the balloon occluder is prolapsed.

FIG. 26C is a cross-sectional view taken at line 26—26 in FIG. 25 when the balloon occluder is prolapsed. For the foam core occluder described with regard to the FIG. 26A, it can be seen that the wall 26 is prolapsed and reduced in overall outside dimension with hooks 14 being in much closer relationship to each other and out of hooking position. When prolapsed, the inflatable balloon occluder can be withdrawn through the lumen 212 of the RF wound closure probe 200. With the balloon occluder prolapsed, the distal end 216 of closure probe 200 is exposed. A plurality of hooks 14' are mounted at the closure probe distal surface 216. The interfunctioning of the hooks 14 and 14' will be described in more detail below.

Figure 27:
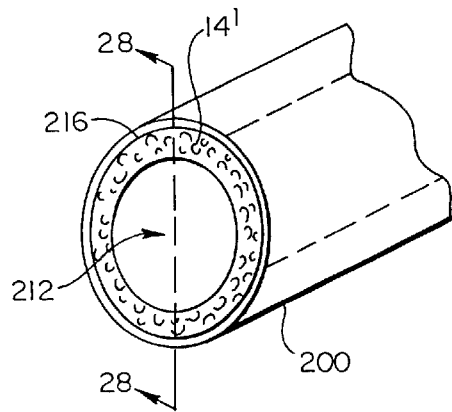
FIG. 27 is a partial schematic diagram of the tip of a closure probe to be used in conjunction with the balloon occluder of FIG. 25.

FIG. 27 is a partial schematic diagram of the tip of the closure probe to be used in conjunction with the balloon occluder of FIG. 25. As illustrated, the distal end 216 has a frustum portion with hooks 14' mounted thereon, the frustum portion surrounding lumen 212.

Figure 28:
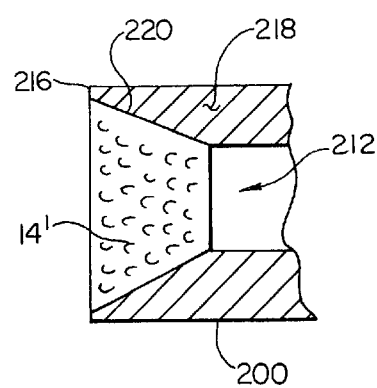
FIG. 28 is a cross-sectional view taken at line 28—28 in FIG. 27.

FIG. 28 is a cross-sectional view taken at line 28—28 in FIG. 27. The outer wall 218 terminates in a frustum section 220 near the distal tip 216 of closure probe 200. Within the frustum portion 220 a plurality of hooks 14' are mounted.

FIG. 29 is a partial schematic diagram of a closing device utilizing the balloon occluder shown in FIG. 25 and the closure probe shown in FIG. 27 encased within a sheath for placement and with portions broken away. The sheath 204 has a first broken away portion 206 exposing the hooks 14 at the proximal end of balloon occluder 190 and the distal end 216 of the RF wound probe 200. Tube 196 passes the length of the closure device and is coupled to pump 222. Pump 222 functions to inflate the occluder 190 or the cause it to prolapse. Controlled pumps are known and are available commercially. An RF source 224 is coupled via wire 226 to a connection point 228 on the RF wound closure probe 200, as illustrated at the second cutaway portion 230. A control 232 shown at broken away section 234 can be utilized to monitor blood flow up the lumen 212 of the closure probe 200. This blood flow, as described above, will occur when the closure device is being located within an artery having a puncture to be closed. It can be used to monitor positioning of the balloon occluder 190, and determine that blood flow stops when occluder 190 has properly closed off blood flow. It can also be used once the closure process has proceeded, as will be described below, to determine that blood flow has remained stopped after the closure process.

FIG. 30A through FIG. 30E are a sequence of partial schematic diagrams that illustrate the interaction of components and the method of closing an aperture utilizing the closing device shown in FIG. 29. Once the closing device has been positioned, as described above, the sheath 204 is withdrawn in the direction of arrow 236, thereby exposing the inflated balloon occluder 190 and its associated hooks 14, as illustrated in FIG. 30A. With the hooks 14 thus exposed, they are positioned to be able to engage the adventitia as described above.

FIG. 30B illustrates the balloon occluder 190 being drawn in the direction of arrow 238 to a proximity of the distal tip of sheath 204, thereby allowing the adventitia to be engaged and hooked as the closure device is withdrawn further in the 25 direction of arrow 238.

FIG. 30C illustrates that when the balloon occluder 190 is rotated in the direction of arrow 240, hooks 14 engage the adventitia. Once the adventitia is engaged by hooks 14, the balloon occluder is moved in the direction of arrow 242 toward the hooks 14' in the distal end 216 of the closure probe 200. The sheath 204 can be removed by withdrawing the direction of arrow 244.

In FIG. 30D, the balloon occluder 190 and the hooked adventitia (not shown) have been moved in the direction of arrow 246 such that the distal end 216 of the closure probe 200 and hooks 14' have engaged the enclosed adventitia. When thus positioned, the closure probe can be rotated in the direction of arrow 248 to cause the hooks 14' to grasp the adventitia and hold it fast.

FIG. 30E illustrates the inflatable balloon occluder 190 in a prolapsed condition and capable of being withdrawn through the lumen 212 of the closure probe 200. When prolapsed, the balloon occluder 190 and its associated hooks 14 will disengage the adventitia and the adventitia will remain engaged by the hooks 14' in the frustum of the closure probe 200. At that time, blood flow will continue to be stopped through the twisted closure of the flaps of the puncture being sealed, and the cauterizing RF power can be applied. Once closed, the closure probe 200 can be reversed in rotation to release the hooks 14', or if the heat sensitive hooks are utilized, the application of the RF power will cause them to straighten and the closure probe can be withdrawn in the direction of arrow 250.

Figure 31:
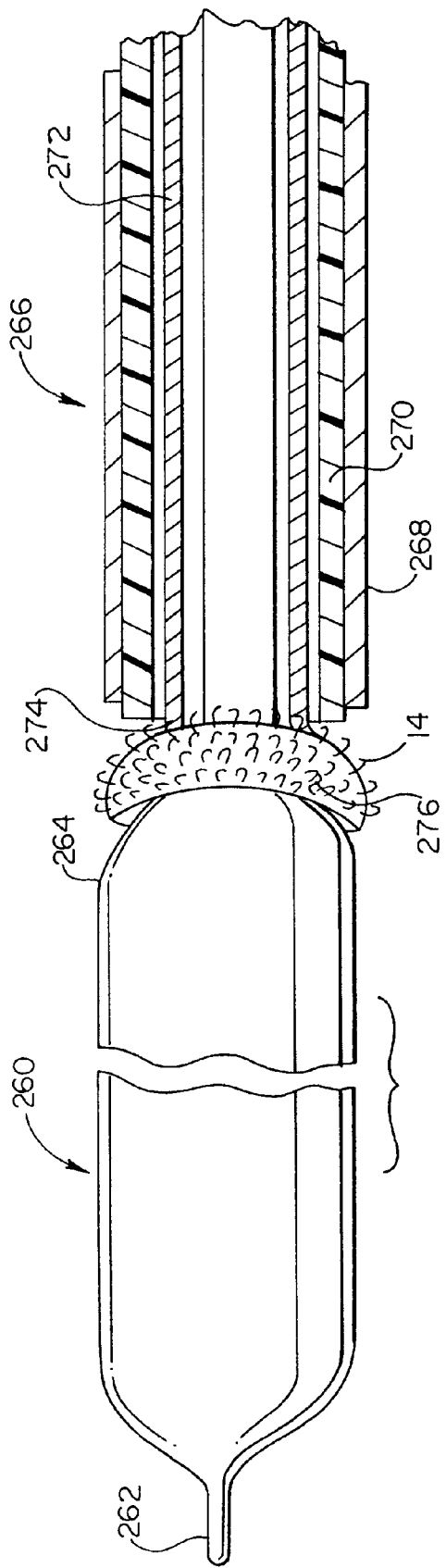
FIG. 31 is a partial schematic diagram of another embodiment of a closing device that utilizes a plurality of hooks elastically mounted to the distal end a closing probe and positioned by expansion of an associated balloon occluder, with parts cross-sectioned.

FIG. 31 is a partial schematic diagram of another embodiment of a closing device that utilizes a plurality of hooks elastically mounted to the distal end of a closing probe and positioned by expansion of an associated balloon occluder, with parts cross-sectioned. In this configuration, the balloon occluder 260 has an atraumatic distal tip 262 and a proximal portion 264. The support member 266 is comprised of an outer Hydrogel member 268 surrounding a flexible tube 270 which can be made of stainless steel, or the like. A plastic sleeve 272 has a distal end 274 to which an elastic material 276 having a plurality of hooks 14 is mounted. The elastic material 276 is of a type that can be suitably stretched by expansion of the balloon occluder 260.

For deployment, the balloon occluder 260 and the support mechanism 266 can be encased in a sheath (not shown) and deployed to within the lumen of the blood vessel having an aperture to be closed. Once deployed, the balloon occluder is inflated, and the distal end 274 of the plastic sleeve 272 is caused to be stretched to match the shape of the proximal end 264 of the balloon occluder 260. This expansion causes the elastic material 276 to stretch and the hooks 14 to be put into a position where they can hook the adventitia when withdrawn. Closure can then be accomplished as described above in the various embodiments, either by way of cauterizing or stasis. Once closure has occurred, the balloon occluder 260 can be prolapsed and withdrawn from the body of the patient.

Figure 32:
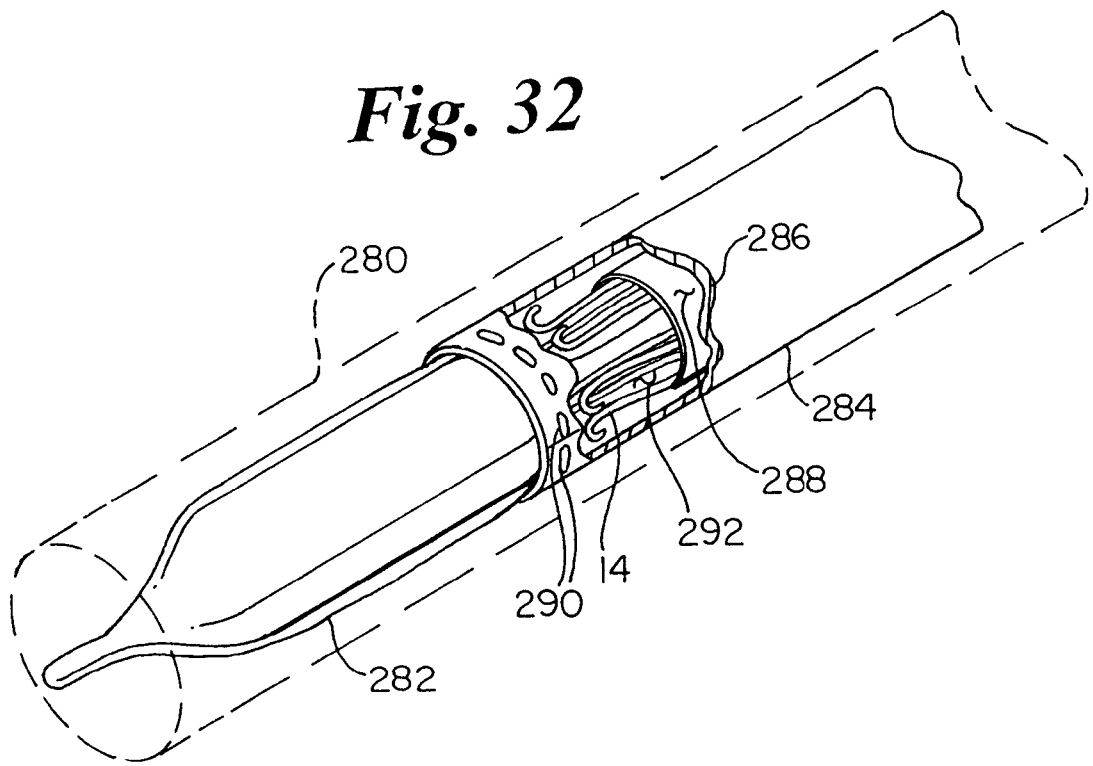
FIG. 32 is a pictorial, schematic diagram of another embodiment of a closing device being deployed and having blood ports for monitoring positioning and effectivity of the closing device.

FIG. 32 is a pictorial, schematic diagram of another embodiment of a closing device being deployed and having blood ports for monitoring positioning and effectivity of the closing device. A sheath is shown in dashed line 280 and encompasses a balloon occluder 282. A closure probe 284 has a portion 286 broken away exposing a plurality of hooks 14 mounted to the inner support member 288. A plurality of blood apertures 290 allow blood to flow into an inner lumen 292 for monitoring blood flow during positioning. When the balloon occluder 282 is not properly positioned, blood will not flow into apertures 290 and the external operator will know that the closing device is not properly positioned. When properly positioned, blood will flow and the balloon occluder 282 can be inflated to allow the closure process to be completed.

Figure 33:
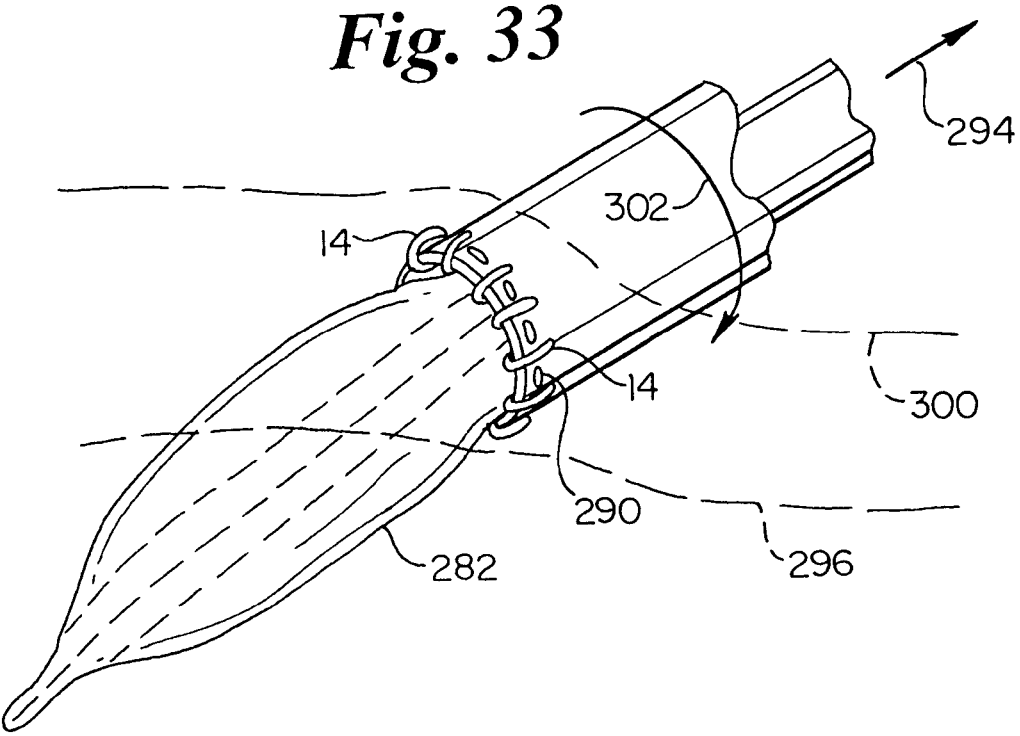
FIG. 33 is a schematic diagram that illustrates the operation of the closing device shown in FIG. 32.

FIG. 33 is a schematic diagram that illustrates the operation of the closing device shown in FIG. 32. In this configuration, apertures 290 will determine whether there is blood flow in the direction of arrow 294. There will be no blood flow when apertures 290 are outside the vessel to be closed. At a minimum, apertures 290 must be outside the media (muscle layer) to assure proper hooking in the adventitia. When dashed line 296 indicates the outside or upper facia of a blood vessel having an aperture to be closed, balloon occluder 282 is partially above the facia line, and no blood will flow into blood ports 290. When thus positioned, the deployed hooks 14 will not be in position to grasp the adventitia beneath the facia and closure cannot occur.

When dashed line 300 is the upper facia of the blood vessel having an aperture to be closed, blood will flow into blood ports 290 and outside of the patient's body. This blood flow will indicate that the closing device is properly placed and the balloon occluder can be inflated. Inflation of the balloon occluder will cause blood flow through blood ports 290 to be stopped, and the closing device can be manipulated to hooks the adventitia and twist it in the direction, for example of arrow 302 in a manner similar to that described above to cause closure of the wound. When thus closed, the balloon occluder 282 can be prolapsed and withdrawn in the direction of arrow 294. When thus removed, the aperture in the blood vessel wall can be closed by stasis or by cauterizing in a manner similar to that described above.

For the foregoing embodiments utilizing the stasis approach to closure, the hooks 14 can be of the configurations described, and can be constructed of suitable plastics such as plastics of the type marketed under the trademark Velcro®, materials that include polymers which absorb water and soften, swell when moistened, collagen fiber, gut suture, elastic fabric, and the like. It is desirable to coat the hooks with a protective coating that is soluble, such as a sugar coating.

Once the hook is placed in the patient's body and exposed to the body fluids, the coating dissolves and the hooks will hydrate and soften thereby causing the hooks to readily disengage without sticking. Closure can be completed as previously described.

Figure 34A:
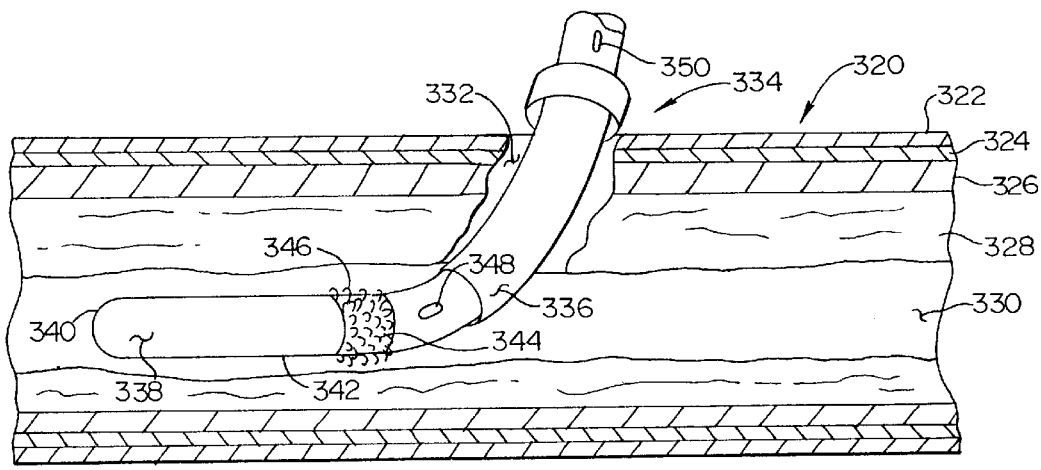
FIG. 34A is a partial cross-sectional view of another embodiment of a closing device that utilizes an elastic closure ring being positioned for closing an aperture in a vessel wall.

FIG. 34A is a partial cross-sectional view of another embodiment of a closing device that utilizes an elastic closure ring being positioned for closing an aperture in a vessel wall. It is of course understood that dimension of the various elements comprising lumen 320 are not to scale, and are shown for illustrative purposes. The vessel 320 is shown cross-sectioned and is comprised an upper wall having the layers including the facia lotta 322, the femoral sheath 324, the adventitia 326, and the media 328 layers. A lumen 330 extends along the length of vessel 320. The upper wall has an aperture 332 therethrough. A deployment device 334 includes a deployment sheath 336 having a length extending from outside the vessel 320, through aperture 332, and available externally to the patient's body for manipulation of the deployment device 334. For positioning, a soft atraumatic foam core tip 328 has a distal tip 340 and a proximal portion 342 over which is deployed an elastic closure ring 344. The elastic closure ring 344 will be described in more detail below, but generally includes a plurality of adventitia engaging hook members on its outer surface, and having a self-adhering inner surface (not shown in FIG. 34A) comprises of a hook and pile structure that adheres with itself when the elastic closure ring 344 is allowed to collapse. For assistance in positioning, a distal blood port 348 is exposed to blood flow in lumen 330 when the outer sheath 336 is withdrawn to expose the atraumatic tip 338, the elastic closure ring 344, and port 348. A longitudinal lumen connects port 338 with output port 350, and is used in positioning the deployment device 334 within aperture 332, as will be described in more detail below.

FIG. 36B is a partial cross-sectional view of the closing device shown in FIG. 36A with blood flow ports indicating positioning of the elastic closure ring within a vessel having an aperture to be closed. Upon withdrawal of the deployment sheath 336 outside the upper wall of vessel 320, a portion of the foam lined delivery handle 352 which was compressed within the side of delivery sheath 336, is exposed and expands to close off aperture 332. When thus positioned, blood can flow in through port 348, and pass through a longitudinal lumen (not shown) to be discharged through port 350 as blood flow 354. When thus positioned, the blood flow indicates that the atraumatic foam core tip 338 and the elastic closure ring 344 are positioned within lumen 330 and are available to be retracted to a closure position.

FIG. 36C is a partial cross-sectional view of the closing device shown in FIG. 36A, with a blood flow port indicating positioning of the elastic closure ring positioned for closing an aperture in a vessel wall. Once blood flow indicates that the closure system is positioned properly, the entire deployment device 334 is withdrawn until the elastic closure ring 344 is in hooking engagement with the adventitia 326. When thus positioned, blood port 348 is outside the boundary of vessel 320, and no blood flow will pass into port 348, nor will any blood flow out of proximal port 350. When thus positioned, the closing action can be accomplished, as will be described in more detail below, and the deployment device 334 totally removed from aperture 332, such that the elastic closure ring 344 can complete the closure operation.

Figure 35:
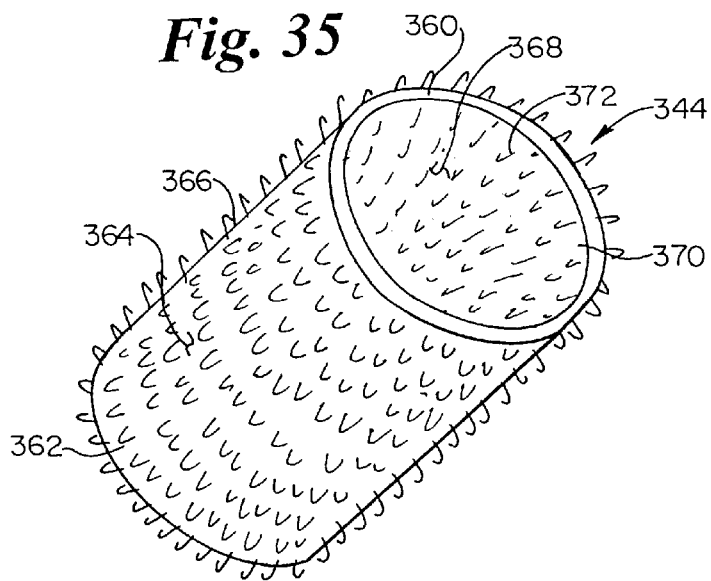
FIG. 35 is a pictorial schematic diagram of another embodiment of a closing device that utilizes an elastic ring having a plurality of hooks mounted on an outer surface and an inner surface having a hook and pile structure to hold the elastic closure ring closed when positioned.

FIG. 35 is a pictorial schematic diagram of another embodiment of a closing device that utilizes an elastic closure ring having a plurality of hooks mounted on an outer surface and an inner surface having a hook and pile structure to hold the elastic closure ring closed when positioned. The elastic closure ring 344 has an upper end 360 and a lower end 362. As shown, it is expanded. An outer surface 364 has a plurality of hooks 366 mounted thereon. As described above, the hooks 366 can be positioned in various adventitia-engaging positions. An inner surface 368 having a plurality of hooks 370 and a plurality of pile elements 372 affixed thereto. The hook and pile structure is such that when the inner surface 368 has any portion brought into contact with itself, the interacting hooks 370 and pile 372 functions to engage. Such engagement causes the various portions of inner surface 368 that interact with each other to be firmly affixed.

The total elastic closure ring 344 is constructed of a bio-absorbable material that is sufficiently stretchable to be mounted on the atraumatic tip 338, while retracting sufficiently to allow interaction locking of the hook and pile structure when the elastic closure ring 344 is removed from the deployment mechanism 334. While it is indicated that the hook 370 and pile 372 elements are shaped differently in the disclosed embodiment, it should be understood that the pile elements 372 can also be a hook structure. It is necessary only that the plurality of elements mounted on the inner surface 368 be of a nature and configuration to interact with itself to form the releasable closure engagement.

Figure 34B:
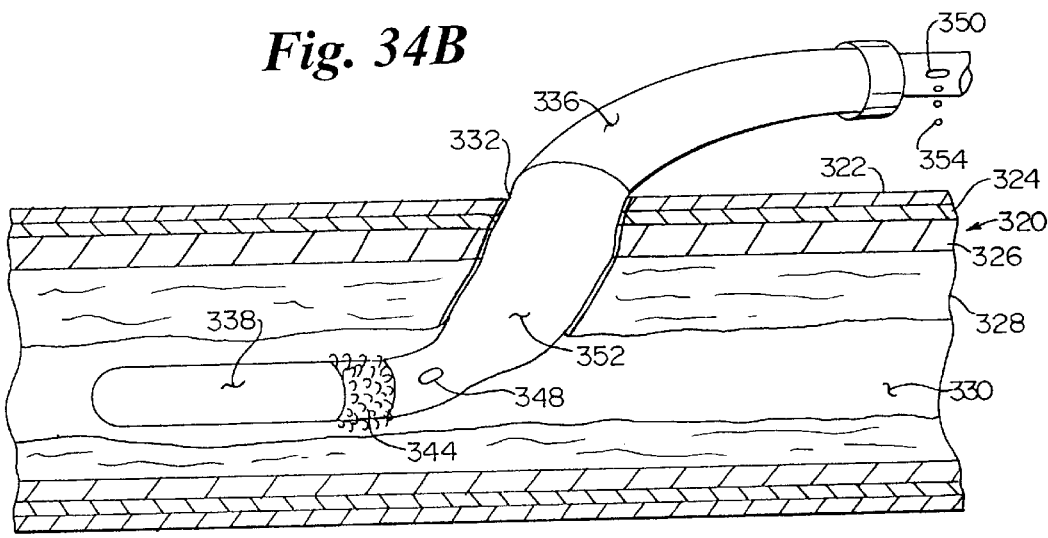
FIG. 34B is a partial cross-sectional view of the closing device shown in FIG. 34A with blood flow ports indicating positioning of the elastic closure ring within a vessel having an aperture to be closed.
Figure 34C:
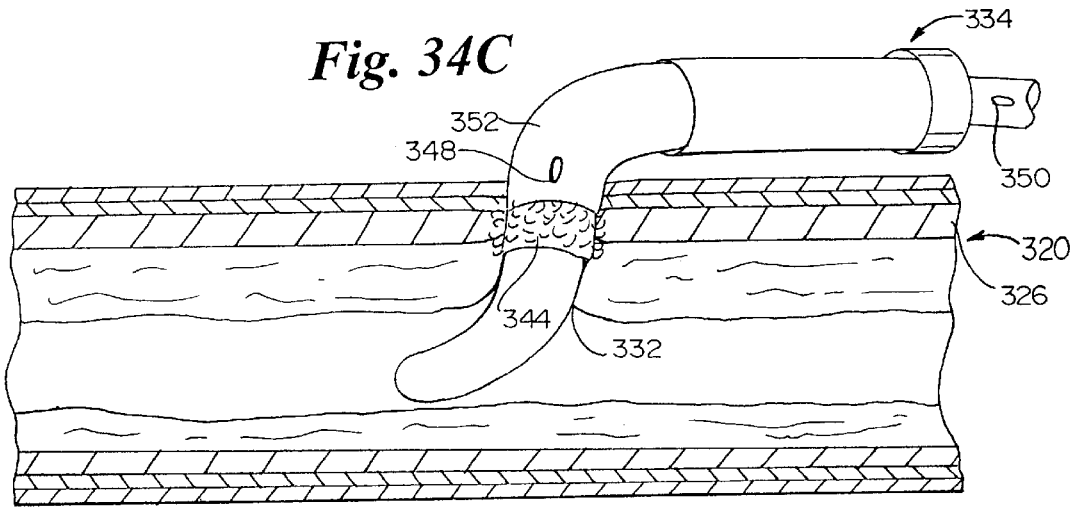
FIG. 34C is a partial cross-sectional view of the closing device shown in FIG. 36A with a blood flow port indicating positioning of the elastic closure ring positioned for closing an aperture in a vessel wall.

FIG. 36A is a partial cross-sectional schematic diagram of the embodiment of the closing device of FIG. 34A illustrating the relationship of the elastic closure ring and the positioning system during the initial positioning process. The outer deployment sheath 380 surrounds the entire deployment mechanism with the exception of the atraumatic positioning tip 382. A delivery handle 384 is compressed within the introducer sheath 380 and can be constructed of an expandable polymer material. With reference back to FIG. 34B, the portion 352 of the delivery handle positioning sheath such that the aperture 332 is sealed by the expanding action. A pair of concentric clamp cylinders comprised of outer clamp cylinder 386 and inner cylinder 388 have distal ends 390 and 392, respectively, that firmly grip a proximal portion 394 of the elastic closure ring 344. When the deployment sheath 380 is positioned as shown, the plurality of hooks 346 are retained within the sheath 380, and the distal blood port 348 is covered. The configuration illustrated would be used during insertion of the total deployment mechanism 334, and would be the configuration immediately preceding that illustrated in FIG. 34A.

FIG. 36B is a partial cross-sectional schematic diagram of the closing device shown in FIG. 36A with the elastic closure ring being deployed to an adventitia-engaging position. In this configuration, the outer deployment sheath 380 has been withdrawn, similar to the placement illustrated in FIG. 34A, and has allowed the proximal portion 396 of the compliant tip 382, to expand and move the elastic closure ring 344 into a stretched position for engaging the adventitia of the aperture to be closed. The concentric cylinders 386 and 388 continue to grip portion 394 of the elastic closure ring 344 in such a manner that it can be manipulated. With the outer sheath 380 withdrawn, the distal blood port 348 is exposed and can be utilized in determining when blood flow stops as the deployment mechanism is withdrawn through the aperture to be closed to a point where the elastic closure ring 344 engages the adventitia of the aperture to be closed.

Figure 37A:
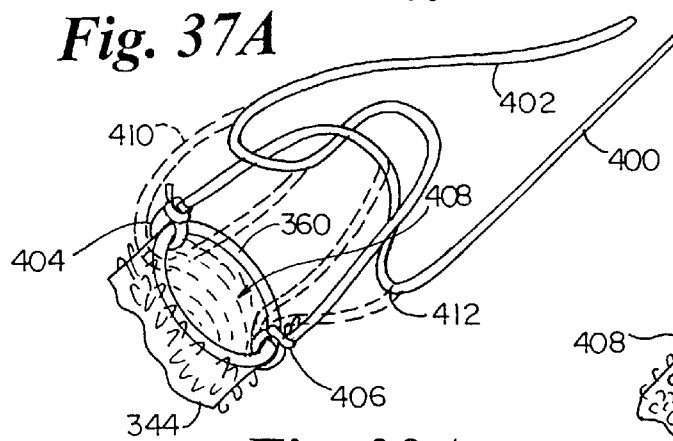
FIG. 37A illustrates suture material coupled to one end of an elastic closure ring.
Figure 37B:
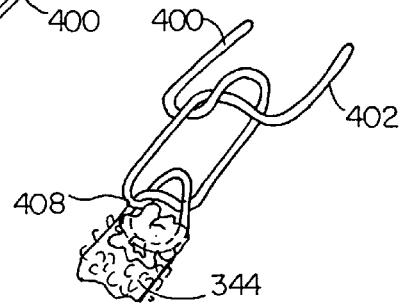
FIG. 37B illustrates the closure ring of FIG. 37A when released and contracted, with the sutures to draw the elastic closure ring closed upon itself.

FIG. 37A illustrates suture material coupled to one end of the elastic closure ring. In order to provide a firm closure of the inner opening of the elastic closure ring 344, suture elements 400 and 402 can be coupled to the upper end 360 such as by couplings 404 and 406, respectively. As thus positioned, the opening indicated by arrow 408 can be drawn closed and knotted to assist in a firm closure of the opening 408. In an alternative configuration, element 400 can be inserted back through the elastic closure ring material as indicated by dashed line 410, and element 402 can be inserted back through the elastic closure ring material as indicated by dashed element 412, to further assist in drawing the top portion 360 together when closure is to be knotted off. The suture elements 400 and 402 can be manipulated from external the patient's body, as can the loops that are utilized to form the closure knot.

FIG. 37D illustrates the closure ring of FIG. 37A when released and contracted, with the sutures to draw the elastic closure ring closed upon itself. As shown, the elastic closure ring 344 has collapsed upon itself, and the central opening 408 is essentially closed. To further assure the closure, the suture elements 400 and 402 are knotted in a manner to pull the opening 408 fully closed, and blood flow is totally stopped.

Figure 38A:
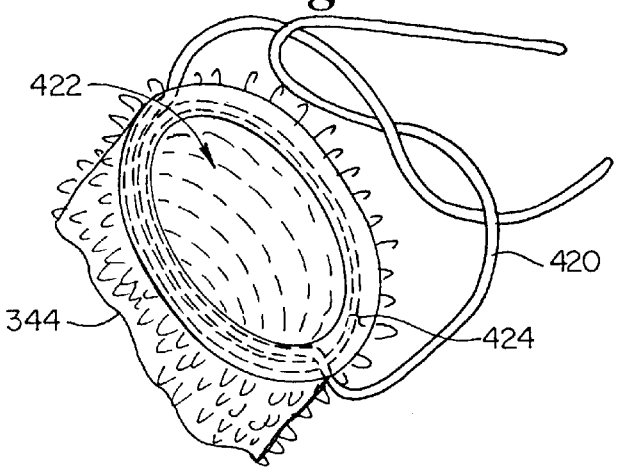
FIG. 38A illustrates suture material slidably retained as drawstrings near one end of an elastic closure ring.

FIG. 38A illustrates suture material slidably retained as drawstrings near one end of an elastic closure ring. As shown, suture material 420 is threaded around openings 422 and is slidably engaged near end 424. The slidable engagement is such that when the suture material 420 applies pressure, the opening 422 can be pulled closed and the suture element 420 knotted to secure the closure.

Figure 38B:
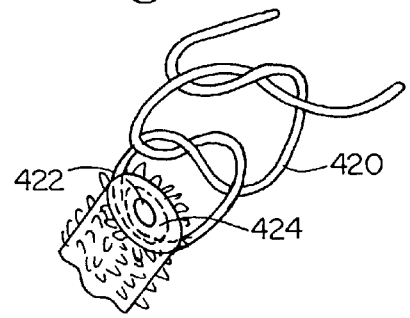
FIG. 38B illustrates the elastic closure ring of FIG. 38A in the closure position with the suture material drawing closed the opening in the elastic closure ring.

FIG. 38B illustrates the elastic closure ring of FIG. 38A in the closure position with the suture material drawing closed, the opening in the elastic closure ring. With the suture material 420 drawn tight, the end 424 is drawn closed, and the central opening 422 is sealed off.

The interaction of the hook and pile inner structure and the suturing and knotting operations results in a tight closure, though in most instances, the hook and pile interlocking structure will be sufficient to cause the requisite aperture closure.

In operation, then the embodiment that utilizes the elastic closure ring can be utilized for closing apertures in the vascular system or punctures or apertures formed in other body organs. Within the vascular system, the deployment device with only the soft atraumatic foam tip exposed, is inserted through the aperture, as described with regard to the FIG. 36A, to a point where the deployment sheath 380 can be withdrawn sufficiently to expose the distal blood port 348. When thus exposed, as described with regard to FIG. 34A and FIG. 34B, blood flow from the proximal blood port 350 will indicate that the distal blood port 348 is within the blood flow stream. Thereafter, withdrawal to a point where the elastic closure ring 344 engages the adventitia 326 surrounding the aperture, will result in stoppage of blood flow. When the adventitia is firmly engaged it can detected as a firm resistance to further withdrawal, and the blood flow will stop. When thus engaged, the inner compressible core can be withdrawn, and blood will again flow through the distended center opening of the elastic closure ring 344 and the lumen formed as the inner manipulation cylinder 388. When blood flow is thus experienced, the manipulation cylinders can be utilized to twist the elastic closure ring 344 into firm engagement with the adventitia. Utilizing the concentric gripping cylinders 386 and 388, the elastic closure ring 344 can be twisted into the adventitia and the aperture to be closed to a point where blood flow will stop. Once blood flow has stopped, the outer gripping cylinder 386 can be withdrawn, thereby releasing engagement with portion 394 of the elastic closure ring 344. See FIG. 36B. When released, the inner gripping cylinder 388 can be manipulated to cause release of the gripping section 394 of the elastic closure ring 344. When thus released, the entire deployment structure is removed from the patient's body. The collapse of the elastic closure ring 344 will result in the hook and pile structure engaging and holding the elastic closure ring in a closed off position. As described above, it may be desirable to utilize the suture elements to knot the closure and firmly hold the hook and pile structure in engagement. As indicated, all of the elements utilized are bio-absorbable and are efficient to quickly and completely close an aperture in the vascular system or in any other body organ for which there has been minimal invasive surgery.

The fabrication of the various hooking and adventitia-engaging elements can be accomplished through a variety of manufacturing functions. As indicated above, the materials selected can either be of the bio-absorbable nature, or can be of various forms of plastics or other materials that require removal from the patient's system. In a basic configuration, a plurality of a number of hooking elements can be affixed to the distal end of a longitudinal support member, as, for example, by gluing or other adhering processes. In another configuration, loops of material can be stitched through a polymer sleeve affixed to the distal end of the positioning mechanism, with the loops then being severed to leave a curved hook-like stubble or bristles. In yet another manufacturing process (not shown in the drawings), an elastomer material can be extruded over the distal portion of the longitudinal support member with radial spikes being formed by pressure molding. To form a hook-like structure, the spikes may be rolled with application of heat such that hooks are formed, and may be biased in any hooking direction desired. Still another method of manufacture (not shown) could utilize the winding loops of selected wire around the distal end of the longitudinal support member with the loops being held down with retention wire. Severing of the loops will result in the formation of curved bristles with no stubble.

Yet another method of manufacture (not shown) would involve the wrapping of individual coils around the longitudinal support member in proximity to the distal end, with an end of each of the coils extending axially. The extending ends can then be rolled or formed into the desired hook structure and biased as required for the particular configuration selected.

From the foregoing, it can seen that the various embodiments and configurations of the invention have achieved the stated objectives.

From the foregoing detailed descriptions of the preferred embodiments and the consideration of the drawings, it can be seen that an improved closure device for closing openings in blood vessel walls has been achieved. The various objectives and purposes are accomplished by positioning hooking means within the lumen of a blood vessel through the aperture or puncture wound to be closed, and withdrawing the hooking means to cause engagement with the collagen fiber in the adventitia. When properly manipulated, the inside-to-outside hooking action can result in the aperture being closed upon itself. Various embodiments of closing devices and methods for causing closure of punctures in blood vessels have been described. The improved closing device in its embodiments improve over the prior art closure systems through certainty of closure, improved functionality, ease of operation, minimization of time required to accomplish the wound closure, reduced cost, and shortened patient recovery time.

It will be understood that this disclosure, in many respects, is only illustrative. Changes may be made in details, particularly in matters of shape, size, material, and arrangement of parts without exceeding the scope of the invention. Accordingly, the scope of the invention is as defined in the appended claims.

What is claimed is:

1. For use in closing an aperture in a body organ having at least a fibrous portion in proximity to the aperture, a closing device comprising:

support means having a distal end for extending through the aperture beyond the fibrous portion in proximity to the aperture to be closed and having a proximal end for selectively providing a first manipulation and a second manipulation;

engaging means mounted at said distal end of said support means, for engaging the fibrous portion in proximity to the aperture, whereby said first manipulation of said support means causes the aperture to be closed by said engaging means; and sealing means for causing the closed aperture to be sealed, wherein said sealing means includes cauterizing means for cauterizing the closed aperture, said sealing means being connected to said support means.

2. A closing device as in claim 1, and further including:

delivering means for delivering said support means and said engaging means to an operative proximity with the aperture, said delivery means being slidably connected to said support means.

3. A closing device as in claim 2, wherein said delivery means includes:

positioning means for locating said engaging means within the aperture.

4. A closing device as in claim 3, wherein said positioning means includes blood flow detecting means for detecting the presence of blood flow during positioning.

5. A closing device as in claim 2, wherein said engaging means include hooks means arranged in a predetermined configuration for responding to said first manipulation to engage the fibrous portion for closing the aperture.

6. A closing device as in claim 5, wherein said hook means includes a plurality of hook members each having at least a flexible portion deflected within said delivery means, for extending said plurality of hooks members beyond said delivery means when said support means is moved within said delivery means.

7. An improved method of closing an aperture in the wall of an blood vessel, wherein the blood vessel has a lumen carrying blood, an outer facia, an adventitia layer, and a media layer, said method comprising the steps of:

a. inserting a plurality of hooks through the aperture into the lumen;

b. extending the plurality of hooks to engage the adventitia layer surrounding the aperture;

c. withdrawing the plurality of hooks through the media layer to engage the adventitia layer;

d. manipulating the plurality of hooks to cause the engaged adventitia to close the aperture; and e. sealing the closed aperture, wherein the step of sealing includes cauterizing the closed aperture.

8. The method of claim 7, wherein the step of sealing includes clamping engaged adventitia between the plurality of hooks and a sealing ring.

9. The method of claim 7, and further including the step of:

occluding the flow of blood from the lumen out through the aperture during steps a–c.

10. The method of claim 7, and further including the step of:

sensing blood flow through the aperture for positioning the plurality of hooks prior to preforming step a.

11. For use in closing an opening in a blood vessel having a lumen carrying blood and collagen fibrous tissue in proximity to the opening, a closing device comprising:

a support member having an outer surface, a proximal end, a distal end, and having a length sufficient to place said distal end in proximity to the opening;

a plurality of hooks mounted in a predetermined pattern on said outer surface in predetermined proximity to said distal end, and adapted to cooperate with and to engage the fibrous tissue when said support member is actuated, wherein said support member includes a compliant inflatable balloon having a predetermined length, a distal atraumatic tip portion, and a proximal portion supporting said plurality of hooks.

12. A closing device as in claim 11, wherein said support member comprises an elongated flexible tube.

13. A closing device as in claim 12, wherein said elongated flexible tube has a diameter up to about 45 F.

14. A closing device as in claim 12, wherein said elongated flexible tube is constructed of stainless steel.

15. A closing device as in claim 11, wherein said plurality of hooks extend outwardly from said outer surface in a predetermined fibrous tissue hooking configuration.

16. A closing device as in claim 15, wherein each of said plurality of hooks is smooth, as a predetermined cross-section, and is adapted to cooperate with and engage the fibrous tissue when moved in a first manner and to release the fibrous tissue when moved in a second manner.

17. A closing device as in claim 15, wherein said plurality of hooks are constructed of atraumatic material selected from the class of materials including flexible plastic, Nitinol, stainless steel, plastic with dissolvable protective coating, hydroplastic and bio-absorbable plastic.

18. A closing device as in claim 11, wherein said plurality of hooks extend outwardly from said proximal portion in predetermined hooking configuration.

19. A closing device as in claims 18, wherein each of said plurality of hooks is smooth, has a predetermined cross-section and is adapted to cooperate with and engage the fibrous tissue when said support member is actuated in a first manner and to release the fibrous tissue when said support member is actuated in a second manner.

20. For use in closing an opening in a blood vessel, the blood vessel having a lumen carrying blood and fibrous tissue in proximity to the opening, a closing device comprising:

a heating element having a distal end, a proximal end, and a tip surface at said distal end;

a support member having a first end coupled to said proximal end and having a length sufficient to position said distal end in proximity to the opening, and a second end to manipulate said heating element; and a plurality of hooks mounted in a predetermined pattern on said tip surface and arranged to engage the fibrous tissue when said second end is manipulated in a first direction and to release the fibrous tissue when said second end is manipulated in a second direction.

21. A closing device as in claim 20, and further including a power circuit coupled to said heating element.

22. A closing device as in claim 21, wherein said power circuit includes a radiofrequency source.

23. A closing device as in claim 22, and further including a delivery mechanism having a distal portion and a proximal portion, said heating element having a first position enclosed within said delivery mechanism until positioned near the opening and said heating element having a second position extending distally of said delivery mechanism.

24. A closing device as in claim 23, wherein said plurality of hooks extend outwardly from said tip surface in a predetermined hooking configuration.

25. A closing device as in claim 24, wherein said plurality of hooks are constructed of atraumatic material selected from the class of materials including flexible plastic, Nitinol, stainless steel, plastic with dissolvable protective coating, hydroplastic and bio-absorbable plastic.

26. A closing device as in claim 24, wherein said plurality of hooks are affixed to said tip surface by heat releasing glue.

27. A closing device as in claim 24, wherein said plurality of hooks are made of bio-absorbable material.

28. A closing device as in claim 24, wherein said plurality of hooks are made of material wherein said plurality of hooks are made of temperature sensitive material wherein each of said plurality of hooks maintains a hooking configuration at a first temperature and relaxes to a substantially straightened releasing configuration at a second temperature.

29. For use in closing an opening in a blood vessel utilizing the adventitia in proximity to the opening, a closing device comprising:

a support mechanism having a distal end, a proximal end, and a predetermined length sufficient to position said distal end through the opening while said proximal end is externally manipulatable;

a plurality of hooks coupled to said distal end, and arranged to engage the adventitia when said support member is manipulated, wherein each of said plurality of hooks includes a hooking portion, a shank portion, and a proximal interconnecting portion; and a closure mechanism to engage said plurality of hooks and close the opening, wherein said closure mechanism includes an annular ring portion having an inner annular surface, a locking structure mounted to said inner annular surface and arranged to cooperate with said shank portion of each of said plurality of hooks, a peripheral surface on said locking structure, a first portion extending outwardly a predetermined distance from said peripheral surface, and a second annular portion extending toward said plurality of hooks.

30. A closing device as in claim 29, wherein said predetermined distance is selected to cause said second annular portion to cooperate with said plurality of hooks to secure adventitia therebetween.

31. A closing device as in claim 30, wherein each said shank portion includes retention protrusions to cooperate with said locking structure.

32. For use in closing an opening in a blood vessel utilizing the adventitia in proximity to the opening, a closing device comprising:

a positioning probe having a distal tip and a predetermined length sufficient to locate said distal tip through the opening, said positioning probe having a longitudinal channel along a predetermined portion of said predetermined length, said longitudinal channel having a proximal opening and a distal opening at said distal tip;

an electrode having a head portion having a distal end and configured to slidably cooperate with said longitudinal channel from said proximal opening to said distal opening, and having a handle portion to manipulate said head portion; and a plurality of hooks mounted on said distal end and arranged to engage the adventitia when said handle portion is manipulated.

33. A closing device as in claim 32, and further including:

a source of radiofrequency power coupled to said electrode to cauterize the closed opening.

34. A closing device for use in closing a perforation in a body organ having fibrous tissue adjacent to at least a portion of the perforation, the closing device comprising:

an elastic material ring having an inner surface, an outer surface, a predetermined length, and first and second ends, said elastic material ring capable of having a stretched position and a relaxed position;

a plurality of fibrous tissue engaging members mounted on said outer surface; and a hook and pile structure mounted on said inner surface.

35. A closing device as in claim 34, and further including a suture mechanism coupled to said elastic material ring.

36. A closing device as in claim 34, wherein said elastic material ring, said plurality of fibrous tissue engaging members, and said hook and pile structure are fabricated from bio-absorbable material.

37. A closing device as in claim 34, and further including:

a positioning device to position said elastic material ring in said stretched position to a location in proximity of the fibrous tissue;

an activation mechanism to cause said plurality of fibrous tissue engaging members to engage the fibrous tissue; and a release mechanism coupled to said activation mechanism to cause said elastic material to be released, thereby allowing said elastic material ring to assume said released position to thereby cause said hook and pile structure to engage, whereby said elastic material ring closes the perforation.

38. A closing device as in claim 37, wherein said elastic material ring further includes suture material coupled thereto, whereby said suture material can be utilized to draw said elastic material ring into a tightly relaxed position to thereby firmly engage said hook and pile structure, whereby the elastic material ring tightly closes the perforation.

39. A closing device as in claim 38, wherein said positioning device includes blood flow ports to allow blood flow to be detected for use in positioning said elastic material ring.

40. For use in closing an opening in a blood vessel having a lumen carrying blood and collagen fibrous tissue in proximity to the opening, a closing device comprising:

a support member having an outer surface, a proximal end, a distal end, and having a length sufficient to place said distal end in proximity to the opening;

a plurality of hooks mounted in a predetermined pattern on said outer surface in predetermined proximity to said distal end, and adapted to cooperate with and to engage the fibrous tissue when said support member is actuated, and further including a closure mechanism, wherein said closure mechanism includes a plurality of engaging members to engage the fibrous tissue when brought in contact by said plurality of hooks, wherein said closure mechanism includes a selectively actuatable electrode.

41. A closing device as in claim 40, wherein said closure mechanism includes a locking ring to lock in cooperation with said plurality of hooks to thereby engage at least the fibrous tissue therebetween.

42. A closing device as in claim 41, wherein said locking ring and said plurality of hooks are bio-absorbable.

43. A closing device as in claim 40, and further including:
- a delivery mechanism having a distal portion and a proximal portion, said delivery mechanism having a positioning mode to encase said plurality of hooks and at least a portion of a said support member to allow insertion of said distal portion of said delivery mechanism and said distal end of said support member through the opening, and said delivery mechanism having a closure mode to expose said plurality of hooks in proximity to the fibrous tissue at the opening to allow said plurality of hooks to be manipulated by said support mechanism for effecting closure of the opening.

44. A closing device as in claim 43, and further including:
- a blood flow detecting structure to aid in positioning said distal portion of said delivery mechanism through the opening into the lumen.

45. For use in closing an opening in a blood vessel utilizing the adventitia in proximity to the opening, a closing device comprising:
- a support mechanism having a distal end, a proximal end, and a predetermined length sufficient to position said distal end through the opening while said proximal end is externally manipulatable;
- a plurality of hooks coupled to said distal end, and arranged to engage the adventitia when said support member is manipulated, wherein each of said plurality of hooks includes a hooking portion, a shank portion, and a proximal interconnecting portion; and
- a closure mechanism to engage said plurality of hooks and close the opening, wherein said proximal interconnecting portion of each of said plurality of hooks is coupled to said support mechanism by dissolvable glue.

46. A closing device as in claim 45, wherein said plurality of hooks and said closure mechanism are fabricated from bio-absorbable plastic.

47. For use in closing an opening in a blood vessel utilizing the adventitia in proximity to the opening, a closing device comprising:
- a support mechanism having a distal end, a proximal end, and a predetermined length sufficient to position said distal end through the opening while said proximal end is externally manipulatable;
- a plurality of hooks coupled to said distal end, and arranged to engage the adventitia when said support member is manipulated, wherein each of said plurality of hooks includes a hooking portion, a shank portion, and a proximal interconnecting portion; and
- a closure mechanism to engage said plurality of hooks and close the opening, wherein said support mechanism includes a plurality of distal connecting members each having a distal interconnection portion, each of said plurality of distal connecting members coupled to a respective one of said plurality of hooks.

48. A closing device as in claim 47, wherein said plurality of distal connecting members are substantially parallely aligned during positioning and are biased to urge said plurality of hooks to a separated position.

49. A closing device as in claim 48, wherein said closure mechanism includes:
- an annular ring portion having an inner annular surface; and
- a locking structure mounted to said inner annular surface, and arranged to cooperate with said shank portion of each of said plurality of hooks.

50. A closing device as in claim 49, wherein said closure mechanism includes:
- a peripheral surface on said locking structure;
- a first annular portion extending outwardly a predetermined distance from said peripheral surface; and
- a second annular portion extending toward said plurality of hooks.

51. A closing device as in claim 50, wherein said predetermined distance is selected to cause said second annular portion to cooperate with said plurality of hooks to secure adventitia therebetween.

52. A closing device as in claim 51, wherein each said shank portion includes retention protrusions.

53. A closing device as in claim 52, wherein said proximal interconnecting portion of each of said plurality of hooks is coupled to said support mechanism by dissolvable glue.

54. A closing device as in claim 48, and further including:
- a positioning mechanism surrounding said support mechanism and said plurality of hooks, said positioning mechanism having a distal end, and adapted to position said plurality of hooks in proximity within the opening; and
- a deployment mechanism within said positioning mechanism and movably positionable along said support mechanism to position said closure mechanism in a closing relationship with said plurality of hooks.

55. A closing device as in claim 54, and further including:
- a releasing mechanism to cooperate with and release said plurality of hooks from said support mechanism.

* * * * *